(12) United States Patent
Yedgar et al.

(10) Patent No.: US 8,916,539 B2
(45) Date of Patent: *Dec. 23, 2014

(54) USE OF LIPID CONJUGATES IN THE TREATMENT OF DISEASE

(75) Inventors: Saul Yedgar, Jerusalem (IL); Miron Krimsky, Jerusalem (IL); Arie Ingber, Petach-Tikua (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 1645 days.

This patent is subject to a terminal disclaimer.

(21) Appl. No.: 11/524,519

(22) Filed: Sep. 21, 2006

(65) Prior Publication Data

US 2007/0078107 A1 Apr. 5, 2007

Related U.S. Application Data

(63) Continuation-in-part of application No. 10/989,607, filed on Nov. 17, 2004, now Pat. No. 7,772,196, and a continuation-in-part of application No. 10/952,496, filed on Sep. 29, 2004, now Pat. No. 7,393,938, which is a continuation-in-part of application No. 09/756,765, filed on Jan. 10, 2001, now Pat. No. 7,034,006.

(60) Provisional application No. 60/174,907, filed on Jan. 10, 2000.

(51) Int. Cl.
| | |
|---|---|
| A01N 43/04 | (2006.01) |
| A61K 31/727 | (2006.01) |
| A61K 31/737 | (2006.01) |
| A61K 31/717 | (2006.01) |
| A61K 31/685 | (2006.01) |
| A61K 31/728 | (2006.01) |

(52) U.S. Cl.
CPC ............ *A61K 31/685* (2013.01); *A61K 31/727* (2013.01); *A61K 31/737* (2013.01); *A61K 31/717* (2013.01); *A61K 31/728* (2013.01)
USPC .......................................................... 514/54

(58) Field of Classification Search
CPC . A61K 31/685; A61K 31/717; A61K 31/727; A61K 31/728; A61K 31/737
USPC ............. 514/42, 53, 54, 56, 61, 62; 536/18.7, 536/20, 21, 22.1, 29.1, 29.13, 123.1
See application file for complete search history.

(56) References Cited

U.S. PATENT DOCUMENTS

| | | | |
|---|---|---|---|
| 4,604,376 A | 8/1986 | Teng | |
| 4,624,919 A | 11/1986 | Kokusho et al. | |
| 4,654,327 A | 3/1987 | Teng | |
| 5,064,817 A * | 11/1991 | Yedgar et al. | 514/78 |
| 5,169,636 A | 12/1992 | Nanba et al. | |
| 5,354,853 A | 10/1994 | Staveski et al. | |
| 5,401,511 A | 3/1995 | Margalit | |
| 5,401,777 A | 3/1995 | Ammon et al. | |
| 5,464,942 A | 11/1995 | Sakurai et al. | |
| 5,470,578 A * | 11/1995 | Aoki et al. | 424/450 |
| 5,512,671 A | 4/1996 | Piantadosi et al. | |
| 5,587,363 A | 12/1996 | Henderson | |
| 5,707,821 A | 1/1998 | Rydel et al. | |
| 5,733,892 A | 3/1998 | Sakurai et al. | |
| 5,785,975 A | 7/1998 | Parikh | |
| 6,022,866 A | 2/2000 | Falk et al. | |
| 6,043,231 A * | 3/2000 | Pruzanski et al. | 514/152 |
| 6,071,532 A | 6/2000 | Chaikof et al. | |
| 6,162,787 A | 12/2000 | Sorgente et al. | |
| 6,171,614 B1 * | 1/2001 | Chaikof et al. | 424/450 |
| 6,180,596 B1 | 1/2001 | Tsao | |
| 6,325,385 B1 | 12/2001 | Iwashita | |
| 6,399,301 B1 | 6/2002 | Hawkins et al. | |
| 6,749,813 B1 | 6/2004 | David | |
| 7,034,006 B2 * | 4/2006 | Yedgar et al. | 514/42 |
| 7,101,859 B2 | 9/2006 | Yedgar et al. | |
| 7,141,552 B2 | 11/2006 | Yedgar et al. | |
| 7,393,938 B2 | 7/2008 | Yedgar | |
| 7,504,384 B2 | 3/2009 | Yedgar et al. | |
| 7,608,598 B2 | 10/2009 | Yedgar | |
| 7,772,196 B2 * | 8/2010 | Yedgar | 514/42 |
| 2004/0087492 A1 | 5/2004 | Yedgar et al. | |

FOREIGN PATENT DOCUMENTS

| | | |
|---|---|---|
| EP | 0236951 | 9/1987 |
| EP | 0529659 | 3/1993 |
| EP | 0581281 | 2/1994 |

(Continued)

OTHER PUBLICATIONS

Greaves et al, Arch Dermatol Res (1988 280 (Supply: S33-S41.*
Liguori et al. (Double-Blind, Randomized Clinical Study Comparing Hyaluronic Acid Cream to Placebo in Patients Treated with Radiotherapy, Radiotherapy and Oncology, vol. 42, pp. 155-161, 1997).*
Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.
Yedgar, S, Lichtenberg, D and Schnitzer, E (2000) "Inhibition of phospholipase A(2) as a therapeutic target" *Biochim Biophys Acta* 1488(1-2):182-7.
Soeda et al (Biochemistry 29:5188-5144) Tissue Plasminogen Activator Catalyzed Lys-Plasminogen Activation on Heparin-Inserted Phospholipid Liposomes.

(Continued)

*Primary Examiner* — Brandon Fetterolf
*Assistant Examiner* — Blaine G Doletski
(74) *Attorney, Agent, or Firm* — Mark S. Cohen; Pearl Cohen Zedek Latzer Baratz LLP

(57) ABSTRACT

This invention provides a method of preventing or treating a dermatologic condition including, inter alia, psoriasis, contact dermatitis, and atopic dermatitis, in a subject, the method includes the step of administering to said subject a compound comprising a lipid or phospholipid moiety bound to a physiologically acceptable monomer, dimer, oligomer, or polymer, and/or a pharmaceutically acceptable salt or a pharmaceutical product thereof, in an amount effective to treat the subject suffering from a dermatologic condition.

22 Claims, 6 Drawing Sheets

(56) References Cited

FOREIGN PATENT DOCUMENTS

| | | |
|---|---|---|
| EP | 0581282 B | 2/1994 |
| EP | 1046394 | 10/2000 |
| JP | 04082893 | 3/1992 |
| JP | 09030970 | 2/1997 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 87 02777 | 5/1987 |
| WO | WO 91/00289 | 1/1991 |
| WO | WO 93/21211 A1 | 10/1993 |
| WO | WO 96/04001 | 2/1996 |
| WO | WO 96/11670 | 4/1996 |
| WO | WO 9628544 | 9/1996 |
| WO | WO9628544 | 9/1996 |
| WO | WO 9701330 | 1/1997 |
| WO | WO9701330 | 1/1997 |
| WO | WO 97/48337 | 12/1997 |
| WO | WO9816198 | 4/1998 |
| WO | WO 9816198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Parish et al (Int. J. Cancer 40: 511-518, "Evidence that sulphated polysaccharides inhibit tumour metastasis by blocking tumour-cell-derived heparanases."

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection". Journ. Of Immunology 2005, vol. 15: 175 (10): 6878-84.

Balsinde Jesus, et al Group V Phospholipase $A_2$-mediated Oletic Acid Mobilization in Lipopolysaccharide-stimulated $P388D_1$ Macrophages; , The Journal of Biological Chemistry, vol. 275, Feb. 18 pp. 4783-4786.

Beck, G., et al (2002) Inhibition of LPS-induced chemokine production in human lund endothelial cells by lipid conjugates achored to the membrane British Journal of Pharmacology 135, 1665-1674.

Schnitzer Edit, et al Interaction of hyacluronic acid-linked phophatidylethonolmine (HyPE) with LDL and its effect on the susceptibility of LDL lips to oxidation; CPL 104 (2000) 149-160. Soeda, et al Biochemistry 29: 5188-5144).

Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.

Cummings, B.S., "Phospholipase A2 as targets for anti-cancer drugs," Biochemical Pharmacology, 74 (2007), pp. 949-959.

Kokotos, G. et al., "Novel 2-Oxoamide Inhibitors of Human Group IVA Phospholipase A2," J. Med. Chem., 2002, 45, pp. 2891-2893.

European Office Action for European Patent Application No. 05 808 267.8 dated Aug. 26, 2013.

Extended European Search Report of European Application No. 05808267.8 issued Mar. 15, 2012.

Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.

Teitelbaum D, Arnon R, Sela M, Rabinsohn Y, Shapiro D., "Sphingomyelin specific antibodies elicited by synthetic conjugates," Immunochemistry. Nov. 1973;10(11):735-43.

Weltzien HU, Matthiessen HP, Meyer-Delius M, Zimmermann F, Rüde E., "Acidic "peptidophospholipids", a new class of hapten-bearing cell surface modifying reagents," Mol Immunol. Sep. 1984;21(9):801-10.

Winger TM, Ludovice PJ, Chaikof EL, "Lipopeptide conjugates: biomolecular building blocks for receptor activating membrane-mimetic structures," Biomaterials. Feb. 1996;17(4):437-41.

Office Action of U.S. Appl. No. 11/220,965 dated Mar. 27, 2008.

Office Action of U.S. Appl. No. 11/598,812 dated Dec. 19, 2008.

Office Action of U.S. Appl. No. 10/989,606 dated Sep. 1, 2009.

Supplementary Search Report of European Application No. 05724186.1 dated Nov. 17, 2009.

Office Action of Japanese Application No. 2001-551427 dated Nov. 20, 2009.

Office Action of U.S. Appl. No. 11/822,423 dated Feb. 3, 2010.

Albini, A, et al (1987) "A rapid in vitro assay for quantitating the invasive potential of tumor cells" *Cancer Res* 47(12):3239-45.

Cabanas, et al (1993) "Ligand intercellular adhesion molecule 1 has a necessary role in activation of integrin lymphocyte function-associated molecule 1" *Proc Natl Acad Sci U S A* 90(12):5838-42.

Dan, P, et al (1998) "Inhibition of type I and type II phospholipase A2 by phosphatidyl-ethanolamine linked to polymeric carriers" *Biochemistry* 37(17):6199-204.

Greaves, MW et al (1988) "Prostaglandins, leukotrienes, phospholipase, platelet activating factor, and cytokines: an integrated approach to inflammation of human skin." *Arch Dermatol Res* 280:S33-41.

Krimsky, M, et al (2000) "Assessment of intestinal permeability in rats by permeation of inulin-fluorescein" *J Basic Clin Physiol Pharmacol* 11(2):143-53.

Krimsky, M, et al (2003) "Amelioration of TNBS-induced colon inflammation in rats by phospholipase A2 inhibitor" *Am J Physiol Gastrointest Liver Physiol* 285(3):G586-92.

Margolis-Nunno, H, et al (1996) "Inactivation by phthalocyanine photosensitization of multiple forms of human immunodeficiency virus in red cell concentrates" *Transfusion* 36(8):743-50.

Murthy, SN, et al (1993) "Treatment of dextran sulfate sodium-induced murine colitis by intracolonic cyclosporin" *Dig Dis Sci* 38(9):1722-34.

Okayasu, I, et al (1990) "A novel method in the induction of reliable experimental acute and chronic ulcerative colitis in mice" *Gastroenterology* 98(3):694-702.

Schmiel, DH et al (1999) "Bacterial phospholipases and pathogenesis" *Microbes Infect* 1(13):1103-12.

Schnitzer, E, et al (1998) "LDL-associated phospholipase A does not protect LDL against lipid peroxidation in vitro" *Free Radic Biol Med* 24(7-8):1294-303.

Schnitzer, E, et al (1999) "The Interaction of hyaluronic-phosphatidylethanolamine with low density lipoprotein (LDL) and its effect on copper induced LDL oxidation" *Biophysical Journal* 76(1): Part 2.

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" *Cancer Res* 47(12):3239-45.

Balsinde, J, Balboa, MA, Yedgar, S and Dennis, EA (2000) "Group V phospholipase A(2)-mediated oleic acid mobilization in lipopolysaccharide-stimulated P388D(1) macrophages" *J Biol Chem* 275(7):4783-6.

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmacol* 135(7):1665-74.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

(56) References Cited

OTHER PUBLICATIONS

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P. and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against Chlamydia trachomatis infection in vitro and modulation of inflammatory response in vivo by membrane-bound glycosaminoglycans" *Microbes Infect* 6(4):369-76.

Davidson, FF, Dennis, EA, Powell, M and Glenney, Jr, JR. (1987) "Inhibition of phospholipase A2 by "Lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

\* cited by examiner

Fig. 1.1: Effect of Compound XXVI on the proliferation of cultured human psoriatic fibroblasts and Swiss 3T3 cells.
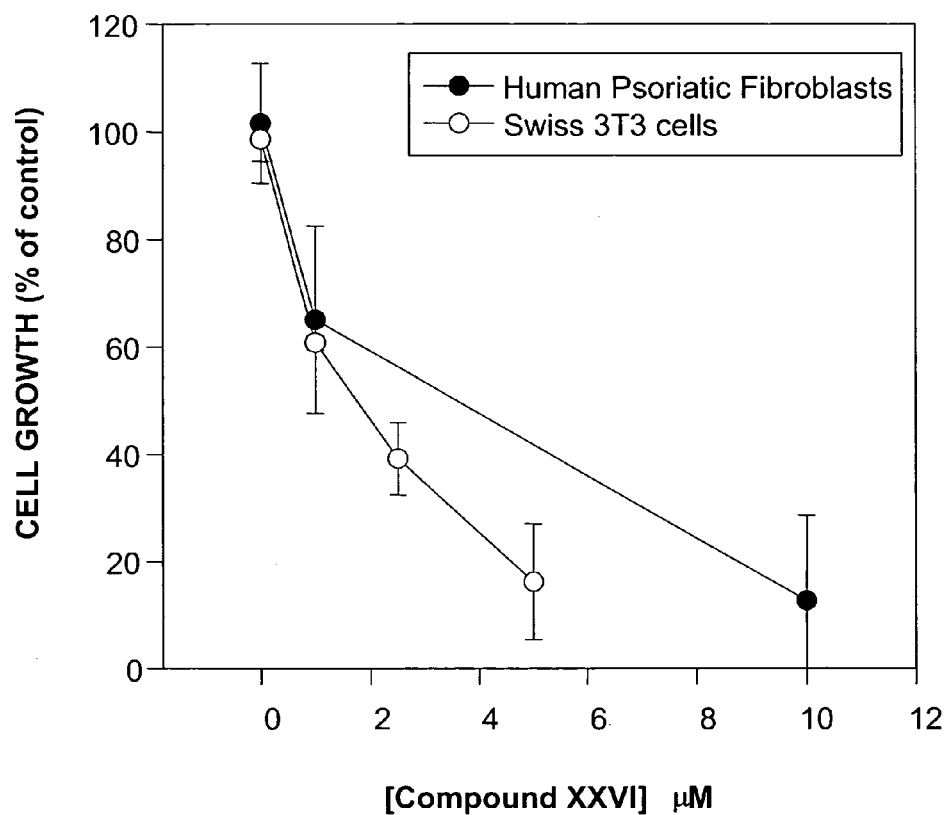

Fig. 1.2: Improvement of contact dermatitis score in patients on vehicle- and Compound XXII -treated sides
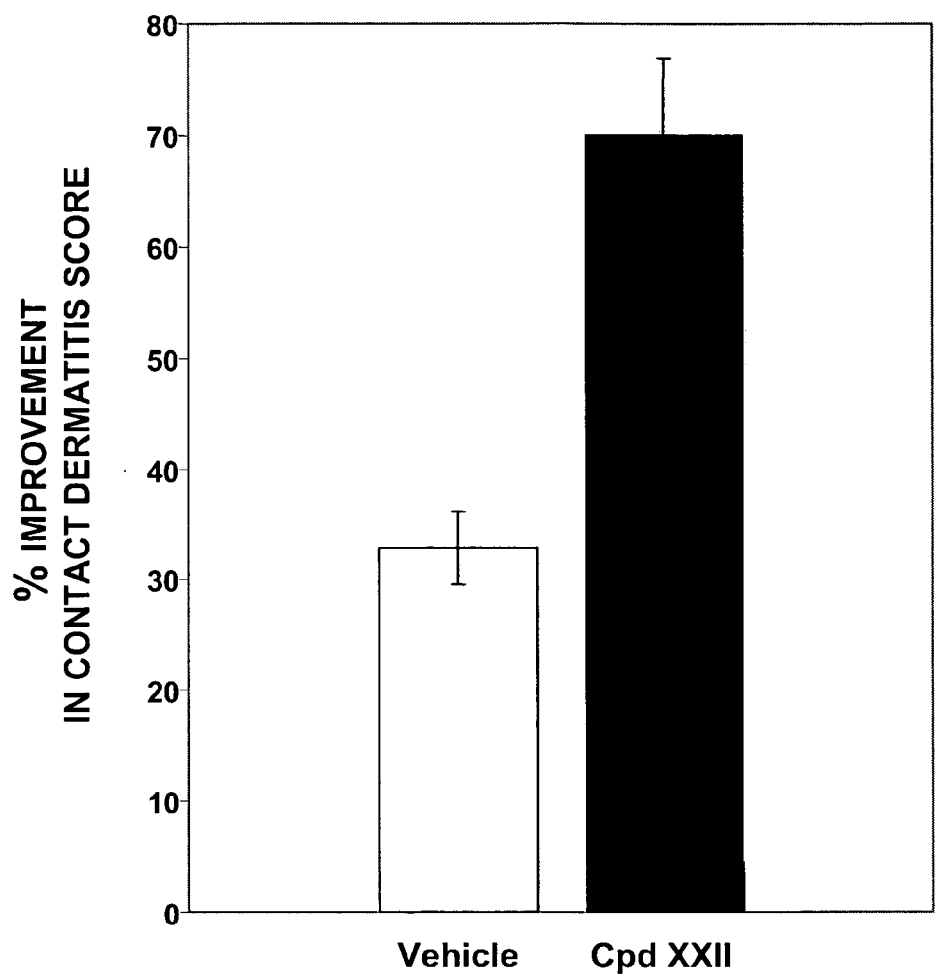

Fig. 2.1: Compound (Cpd) XXVI protects BGM cells from membrane lysis induced by combined action of hydrogen peroxide produced by glucose oxidase (GO) and exogenous phospholipase $A_2$ ($PLA_2$).
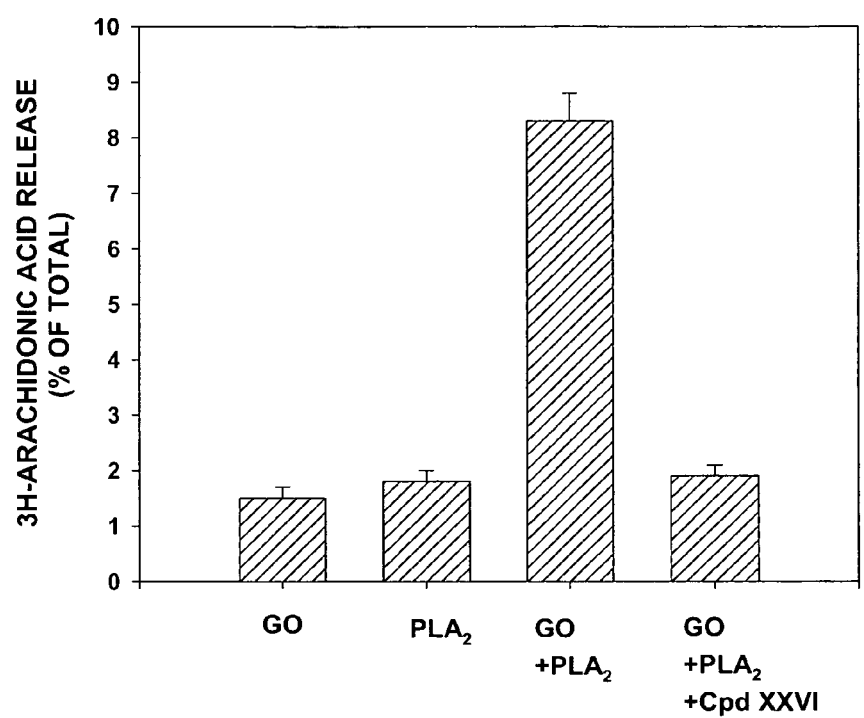

Fig. 2.2: Compound (Cpd) XXVI protects BGM cells from glycosaminoglycan degradation by hydrogen peroxide produced by glucose oxidase (GO).
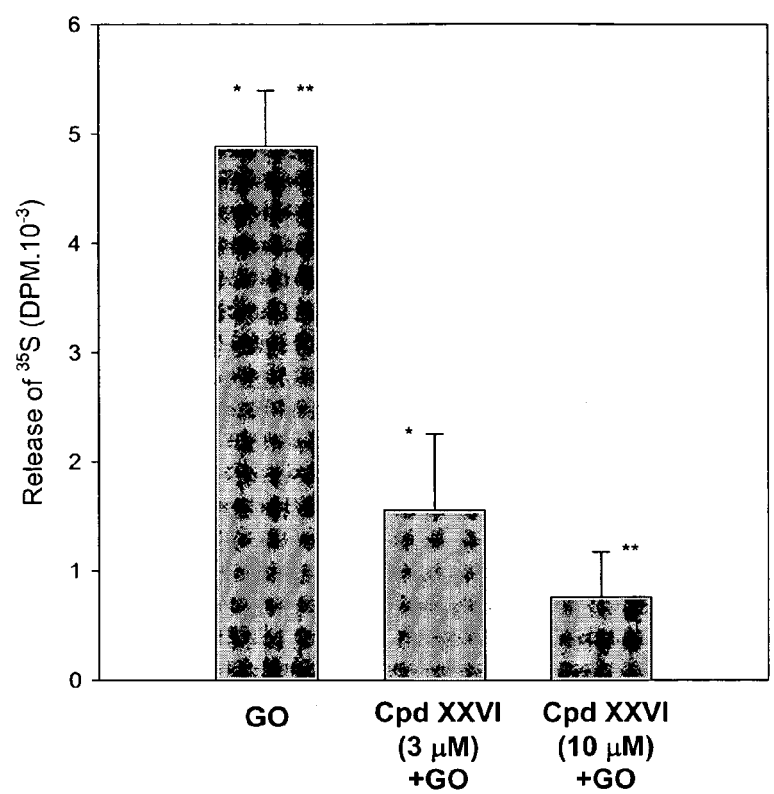

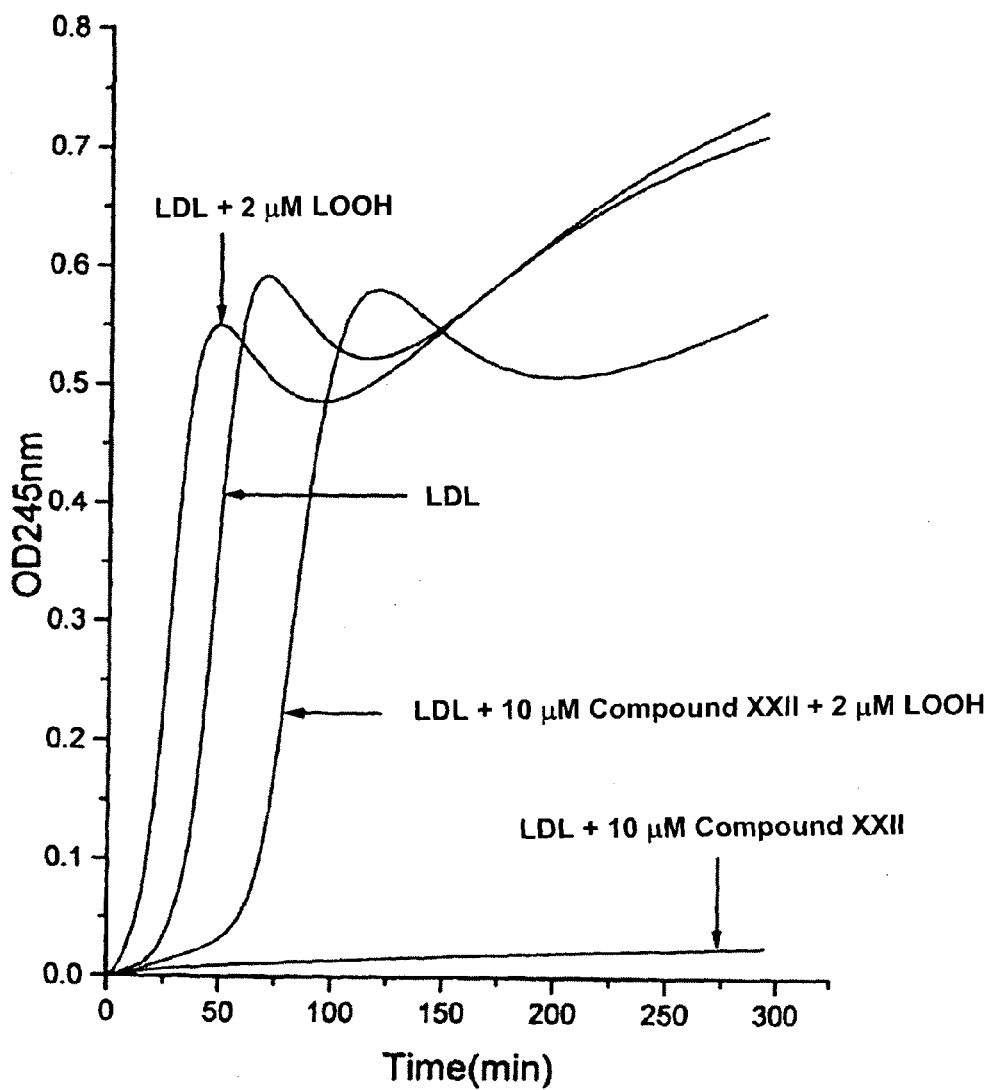
Fig. 2.3: Compound XXII protects LDL from copper-induced oxidation.

Fig. 4.1A: Inhibition of the $PLA_2$ enzyme by Compound XXII
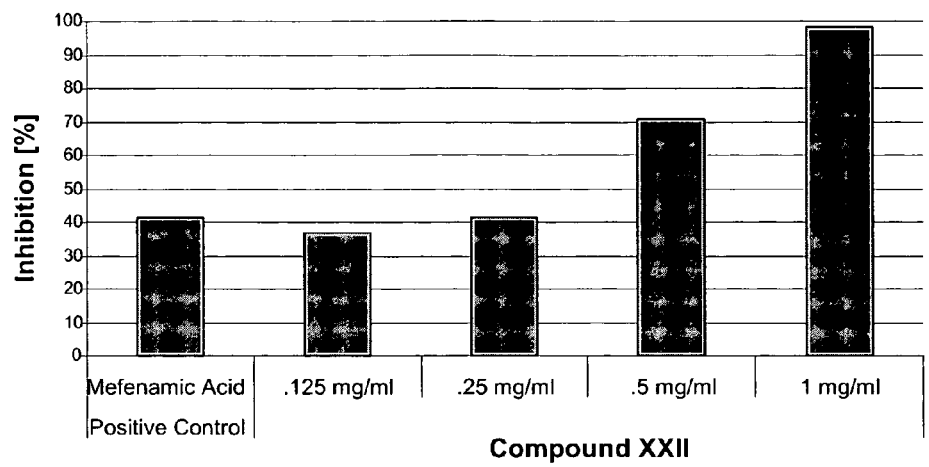
Fig. 4.1B: Inhibition of the $PLA_2$ enzyme by Compound XXV
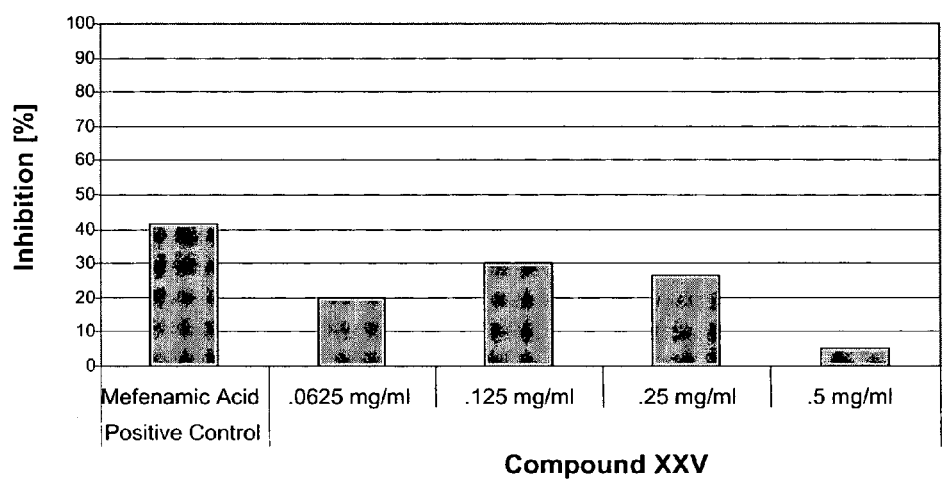

USE OF LIPID CONJUGATES IN THE TREATMENT OF DISEASE

CROSS REFERENCE TO RELATED APPLICATIONS

This application is a continuation-in-part application of U.S. patent application Ser. No. 10/989,607, filed Nov. 17, 2004 now U.S. Pat. No. 7,772,196 and U.S. patent application Ser. No. 10/952,496, filed Sep. 29, 2004, now U.S. Pat. No. 7,373,938 which are continuation-in-part applications of U.S. patent application Ser. No. 09/756,765, filed Jan. 10, 2001, now U.S. Pat. No. 7,034,006 which claims priority from U.S. Provisional Patent Application Ser. No. 60/174,907, filed Jan. 10, 2000, which are hereby incorporated by reference.

FIELD OF THE INVENTION

This invention provides compounds and methods of use thereof in suppressing, inhibiting, preventing, or treating a dermatologic condition in a subject, including, inter alia, psoriasis, contact dermatitis, atopic dermatitis, and seborrheic dermatitis.

BACKGROUND OF THE INVENTION

Lipid-conjugates are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of dermatologic conditions.

Dermatologic conditions are far more prevalent than once thought and cost an estimated $37.17 billion annually in the US, according to a comprehensive study jointly released in April 2005 by the American Academy of Dermatology Association and the Society for Investigative Dermatology. These estimates consider the costs of doctor visits, over-the-counter and prescription medicine costs and lost work productivity. The new study found that at any given time, one in every three people in the U.S. suffers from a skin disease—exceeding the prevalence of obesity, hypertension and cancer. Among the most economically burdensome skin disorders are skin ulcers and wounds, melanoma, nonmelanoma skin cancer, atopic dermatitis and acne, the cost of which totaled $22.46 billion in 2004. It is estimated that NIH research expenditures on skin diseases will total nearly $172 million in 2005.

Dermatitis, which is sometimes called eczema, is an inflammation reaction of the skin to various external and internal causes and is the most common among the skin diseases. Typical clinical features in acute stage dermatitis include swelling erythema, followed by the formation of papules and serous papules on the erythema. After the formation of vesicles in the skin, pustules form, followed by the erosion, crusting and desquamation of the skin. Only then does the skin begin to heal. When dermatitis turns chronic, thickening, lichenification and pigmentation of the skin all result and, in most cases, accompanied by itching. Histologically, dermatitis is characterized by swelling among epidermal cells (in a spongy state) during the acute stage. Contact dermatitis, atopic dermatitis, seborrheic dermatitis, etc. are included among recognized categories of dermatitis.

External application of a steroidal agent (ointment or the like) is the most effective therapy to date and no therapeutic method to replace it has yet been established. However, steroid preparations also cause a great variety of adverse reactions. There have been various reports on the side effects of steroid preparations and, in the case of agents for external use such as ointments, direct harmful effects such as the thinning, shrinking and flushing of the skin. The severe adverse reactions caused by steroid preparations used as remedies for dermatologic conditions have led to a demand in the medical field for safer pharmaceuticals which have fewer side effects.

SUMMARY OF THE INVENTION

In one embodiment, the invention provides a method of preventing a dermatologic condition in a subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof.

In another embodiment, the invention provides a method of treating a dermatologic condition in a human subject, comprising the step of administering to said subject a compound represented by the structure of the general formula (A):

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000;
and/or a pharmaceutically acceptable salt or a pharmaceutical product thereof, wherein X is hyaluronic acid and L is phosphatidylethanolamine.

In one embodiment, X in general formula (A) represents a polysaccharide. In one embodiment, the polysaccharide is carboxymethylcellulose, in another embodiment, the polysaccharide is dextran, while in another embodiment, the polysaccharide is a glycosaminoglycan. In one embodiment, the glycosaminoglycan is hyaluronic acid, in another embodiment, the glycosaminoglycan is chondroitin sulfate, while in another embodiment, the glycosaminoglycan is heparin. In one embodiment, L in general formula (A) is phosphatidylethanolamine, which in one embodiment is dipalmitoyl phosphatidylethanolamine and in another embodiment is dimyristoyl phosphatidylethanolamine.

In one embodiment, the dermatologic condition is a dermatologic disease. In another embodiment, the dermatologic condition is psoriasis. In another embodiment, the dermatologic condition is contact dermatitis. In another embodiment, the dermatologic condition is seborrheic dermatitis. In another embodiment, the dermatologic condition is atopic dermatitis.

BRIEF DESCRIPTION OF FIGURES

FIG. 1.1: Effect of Compound XXVI on the proliferation of cultured human psoriatic fibroblasts and Swiss 3T3 cells.

FIG. 1.2: Improvement of contact dermatitis score on vehicle- and Compound XXII-treated hands.

FIG. 2.1: A Lipid-conjugate protects BGM cells from membrane lysis induced by combined action of hydrogen peroxide produced by glucose oxidase (GO) and exogenous phospholipase $A_2$ (PLA$_2$).

FIG. 2.2: A Lipid-conjugate protects BGM cells from glycosaminoglycan degradation by hydrogen peroxide produced by glucose oxidase (GO).

FIG. 2.3: A Lipid-conjugate protects LDL from copper-induced oxidation.

FIG. 4.1A: Inhibition of the PLA$_2$ enzyme by Compound XXII.

FIG. 4.1B: Inhibition of the PLA$_2$ enzyme by Compound XXV.

DETAILED DESCRIPTION OF THE INVENTION

In another embodiment, the invention provides a method of treating a dermatologic condition in a human subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof.

In another embodiment, the invention provides a method of treating a dermatologic condition in a human subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof, wherein X is hyaluronic acid and L is phosphatidylethanolamine.

In one embodiment, the invention provides a method of preventing a dermatologic condition in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof.

In another embodiment, the invention provides a method of preventing or treating contact dermatitis in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof.

In another embodiment, the invention provides a method of preventing or treating atopic dermatitis in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a physiologically acceptable monomer, dimer, oligomer, or polymer; and
n is a number from 1 to 1000,
and/or a pharmaceutically acceptable salt or a pharmaceutical product thereof.

In one embodiment, X in general formula (A) represents a polysaccharide. In one embodiment, the polysaccharide is carboxymethylcellulose, in another embodiment, the polysaccharide is dextran, while in another embodiment, the polysaccharide is a glycosaminoglycan. In one embodiment, the glycosaminoglycan is hyaluronic acid, in another embodiment, the glycosaminoglycan is chondroitin sulfate, while in another embodiment, the glycosaminoglycan is heparin. In one embodiment, L in general formula (A) is phosphatidylethanolamine, which in one embodiment is dipalmitoyl phosphatidylethanolamine and in another embodiment is dimyristoyl phosphatidylethanolamine.

In one embodiment, the methods of the present invention may be used to prevent or treat any dermatologic condition. In one embodiment, a dermatological condition is a dermatologic disease, which in one embodiment is dermatitis. In one embodiment, dermatitis is referred to as eczema. In another embodiment, the dermatologic condition is contact dermatitis, which in one embodiment is allergic contact dermatitis and in another embodiment is irritant contact dermatitis. In another embodiment, the dermatologic condition is atopic dermatitis, which in another embodiment is infantile eczema, Besnier's prurigo, allergic dermatitis, flexural eczema, or disseminated neurodermatitis. In another embodiment, the dermatologic condition is seborrheic (or seborrhoeic) dermatitis, which in one embodiment is infantile seborrheic dermatitis, while in another embodiment, it's adult seborreic dermatitis. In another embodiment, the dermatologic condition is psoriasis. In another embodiment, a dermatologic condition is: neurodermatitis, scabies, systemic dermatitis, dermatitis herpetiformis, perioral dermatitis, discoid eczema, Nummular dermatitis, Housewives' eczema, Pompholyx dyshidrosis, Recalcitrant pustular eruptions of the palms and soles, Barber's or pustular psoriasis, Generalized Exfoliative Dermatitis, Stasis Dermatitis, varicose eczema, Dyshidrotic eczema, Lichen Simplex Chronicus (Localized Scratch Dermatitis; Neurodermatitis), Lichen Planus, Fungal infection, which in one embodiment may be Candida intertrigo, tinea capitis, white spot, panau, ringworm, athlete's foot, moniliasis, candidiasis; dermatophyte infection, vesicular dermatitis, chronic dermatitis, spongiotic dermatitis, dermatitis venata, Vidal's lichen, asteatosis eczema dermatitis, autosensitization eczema, or a combination thereof.

In another embodiment, the methods of the present invention may be used to prevent or treat pimples, acne vulgaris, birthmarks, freckles, tattoos, scars, burns, sun burns, wrinkles, frown lines, crow's feet, café-au-lait spots, benign skin tumors, which in one embodiment, is Seborrhoeic keratosis, Dermatosis papulosa nigra, Skin Tags, Sebaceous hyperplasia, Syringomas, Xanthelasma, or a combination thereof; benign skin growths, viral warts, diaper candidiasis, folliculitis, furuncles, boils, carbuncles, fungal infections of the skin, guttate hypomelanosis, hair loss, impetigo, melasma, molluscum contagiosum, rosacea, scapies, shingles, erysipelas, erythrasma, herpes zoster, varicella-zoster virus, chicken pox, skin cancers, which in one embodiment, may be squamos cell carcinoma, basal cell carcinoma, malignant melanoma; premalignant growths, which in one embodiment may be congenital moles, actinic keratosis; urticaria, hives, vitiligo, Ichthyosis, Acanthosis Nigricans, Bullous Pemphigoid, Corns and Calluses, Dandruff, Dry Skin, Erythema Nodosum, Graves' Dermopathy, Henoch-Schönlein Purpura, Keratosis Pilaris, Lichen Nitidus, Lichen Planus, Lichen Sclerosus, Mastocytosis, Molluscum Contagiosum, Pityriasis Rosea, Pityriasis Rubra Pilaris, PLEVA, or Mucha-Habermann Disease, Epidermolysis Bullosa, Seborrheic Keratoses, Stevens-Johnson Syndrome, Pemphigus, or a combination thereof.

In another embodiment, the methods of the present invention may be used to prevent or treat insect bites or stings, which in one embodiment comprise mosquito, tick, louse, flea, bed bug, which in one embodiment is *Cimex lectularius* or *Cimex hemipterus* in warmer areas, ant, snake, lizard (which in one embodiment are Gila monster *Heloderma suspectum* or the beaded lizard *H. horridum*), spider, Black Widow Spider, Brown Recluse, Mite, Scorpion bites, or the like, or the skin reaction that is secondary to such bites. In one embodiment, stings comprise Bee, Honey Bee, Hornet, Wasp, or Yellow Jacket stings. In another embodiment, the methods of the present invention may be used to prevent or treat bites or stings from marine animals, including Coelenterates, including the corals, sea anemones, jellyfishes, and hydroids (eg, Portuguese man-of-war); stingrays; mollusks, including the cones, which is one embodiment is *Conus californicus*, octopuses, and bivalves; and Echinoderms and sea urchins which in one embodiment are *Globiferous pedicellariae*.

In another embodiment, the methods of the present invention may be used to prevent or treat dermatologic conditions that are associated with the eye area, which in one embodiment may be Syringoma, Xanthelasma, Impetigo, atopic dermatitis, contact dermatitis, or a combination thereof; the scalp, fingernails, which in one embodiment may be infection by bacteria, fungi, yeast and virus, Paronychia, or psoriasis; mouth area, which in one embodiment is Oral Lichen Planus, Cold Sores (Herpetic Gingivostomatitis), Oral Leukoplakia, Oral Candidiasis, or a combination thereof; or a combination thereof. In one embodiment, the methods of the present invention may be used to prevent or treat dermatologic conditions in babies, infants, toddlers, young children, older children, adolescents, young adults, adults, elderly, or a combination thereof.

It is to be understood that the methods of the present invention may be used to prevent or treat any inflammatory skin condition.

In one embodiment, "preventing, or treating" refers to any one or more of the following: delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics. In one embodiment, "treating" refers to both therapeutic treatment and prophylactic or preventative measures, wherein the object is to prevent or lessen the targeted pathologic condition or disorder as described hereinabove.

In one embodiment, the compounds for use in the methods of the present invention may be used to address the symptoms of a dermatologic condition, which in one embodiment are primary, while in another embodiment, are secondary to the dermatologic condition. In one embodiment, "primary" refers to a symptom that is a direct result of the dermatologic condition, while in one embodiment, "secondary" refers to a symptom that is derived from or consequent to a primary cause.

In another embodiment, "symptoms" may be any manifestation of a disease or pathological condition, comprising inflammation, swelling, superficial skin inflammation, presence of vesicles, poorly marginated redness, red skin, dry skin, thick skin, leathery skin, edema, oozing, crusting, scaling, burning, stinging, pruritus, itching, lichenification, blisters, papules, vesicles, bullae, blisters, tenderness, skin lesion, which in one embodiment, may be oozing, draining, crusting, scaly, raw, thickened or a combination thereof, rash, fever, pain, bleeding or a combination thereof.

As described hereinabove, in one embodiment, the methods of the present invention prevent or treat contact dermatitis. In one embodiment, contact dermatitis is an inflammation produced by substances contacting the skin and causing toxic (irritant) or allergic reactions. In one embodiment, contact dermatitis is initiated by plants (in one embodiment, poison ivy, poison oak, etc.), sensitizers used in the manufacture of shoes and clothing, metal compounds, dyes, cosmetics, industrial agents, rubber accerators, latex goves, latex condoms, ingredients in topical drugs. In one embodiment, contact dermatitis is photoallergic or phototoxic contact dermatitis in which topically applied dermatitides evoke a response after being exposed to light. In one embodiment, aftershave lotions, sunscreens, and topical sulfonamides are commonly responsible for photoallergic contact dermatitis. In another embodiment, perfumes, coal tar, psoralens, and oils used in manufacturing are commonly responsible for phototoxic contact dermatitis. In one embodiment, symptoms of contact dermatitis comprise transient redness, swelling, bullae, erythema, blisters, vesicles which may rupture, ooze, or crust, scaling, skin thickening, acute inflammation, chronic inflammation, or a combination thereof.

As described hereinabove, in one embodiment, the methods of the present invention prevent or treat atopic dermatitis, which in one embodiment, is chronic, pruritic, superficial inflammation of the skin, frequently associated with a personal or family history of allergic disorders (e.g., hay fever, asthma). In one embodiment, susceptibility to atopic dermatitis is genetic, is triggered by environmental agents and factors, is auto-immune, or a combination thereof. In one embodiment, sufferers of atopic dermatitis have high serum levels of reaginic (IgE) antibodies, peripheral eosinophilia, high levels of cAMP phosphodiesterase in their white blood cells, or a combination thereof. In one embodiment, symptoms of atopic dermatitis in infants comprise red, weeping, and/or crusted lesions on the face, scalp, diaper area and extremities. In another embodiment, symptoms comprise erythema, lichenification in the antecubital and popliteal fossae and on the eyelids neck, or wrists, pruritus, atopic pleat (Dennie-Morgan fold), hyperlinear palms, hyperpigmented eyelids, ichthyosis, keratosis pilaris, urticaria, or a combination thereof. In one embodiment, atopic dermatitis appears with and/or may be influenced by secondary bacterial infections, regional lymphadenitis, contact dermatitis from topical allergens, emotional stress, ambient temperature and/or humidity changes, fragrances, fabric softeners, wool garments, house mites, or a combination thereof.

As described hereinabove, in one embodiment, the methods of the present invention prevent or treat seborrheic dermatitis, which in one embodiment is an inflammatory scaling disease or the scalp, face, or other areas with high densities or large oil glands. In one embodiment, symptoms of seborrheic dermatitis comprise dry or greasy diffuse scaling of the scalp (dandruff) with variable pruritus, yellow-red scaling papules along the hairline, behind the ears, in the external auditory canals, on the eyebrows, on the bridge of the nose, in the nasolabial folds over the sternum, or a combination thereof, marginal blepharitis with dry yellow crusts, conjunctival irritation, or a combination thereof. In one embodiment, seborrheic dermatits in newborns may be called cradle cap and, in one embodiment comprises symptoms of thick, yellow, crusted scalp lesion, fissuring, yellow scaling behind the ears, red facial papules, stubborn diaper rash, or a combination thereof. In one embodiment, genetic factors, emotional or physical stress, climate, season, or a combination thereof may affect onset or progression of symptoms. In one embodiment, seborrheic dermatitis may precede or be associated with the development of psoriasis. In one embodiment, the methods of the present invention prevent or treat seborrheic dermatitis in patients with neurologic disease (in one embodiment, Parkinson's Disease) or Human Immunodeficiency Virus (HIV).

As described hereinabove, in one embodiment, the methods of the present invention prevent or treat psoriasis, which, in one embodiment, is a noncontagious inflammatory skin disease characterized by recurring reddish patches covered with silvery scales. In one embodiment, the thick scaling is attributed to increased epidermal cell proliferation and concomitant dermal inflammation. In some embodiments, the methods of the present invention may treat psoriatic arthritis, erythrodermic psoriasis, or pustular psoriasis, which in one embodiment may be von Zumbusch type psoriasis, Palmoplantar pustulosis, Acropustulosis (acrodermatitis continua of Hallopeau), or Barber's psoriasis. In one embodiment, the methods of the present invention prevent or treat plaque psoriasis, guttate psoriasis, inverse psoriasis, erythrodermic psoriasis, a combination thereof, or other forms of psoriasis that are known in the art. In one embodiment, symptoms of psoriasis comprise sharply demarcated lesions, variously pruritic lesions, ovoid or circinate erythematous papules, plaques covered with overlapping thick silvery micaceous or slightly opalescent shiny scales, papules that extend and coalesce to produce large plaques in annular and gyrate patterns, stippling, pitting, fraying, discoloration or separation of the distal and/or lateral margins of the nail plate (onycholysis), thickening, with hyperkeratotic debris under the nail plate, or a combination thereof. In one embodiment, psoriasis has chronic remissions and recurrences that vary in frequency and duration. In one embodiment, factors that precipitate the onset or severity of psoriasis include local trauma, irritation, severe sunburn, viremia, allergic drug reactions, topical and systemic drugs (which in one embodiment comprise chloroquine antimalarial therapy, lithium, β-blockers, interferon-α, or a combination thereof), withdrawal of systemic corticosteroids, or a combination thereof. In one embodiment, psoriasis is found on the scalp (in one embodiment, the postauricular regions), extensor surface of extremities (in one embodiment, elbows, knees, or a combination thereof), face, nails, sacral area, buttocks, genitals, or combination thereof.

In one embodiment, the methods of the present invention may be used to treat a dermatologic condition in a subject that is immunosuppressed, while in another embodiment, in a subject that is immunodeficient.

In one embodiment, the methods of the present invention may be used to treat a dermatologic condition in a subject of any species, which in one embodiment is a mammal, while in another embodiment, the subject is non-mammalian. In one embodiment, the subject is a vertebrate. In one embodiment, the subject is a human. In other embodiments the subject is a primate, equine, avian, bovine, ovine, caprine, porcine, canine, feline or murine subject.

In one embodiment, the methods of the present invention may be used to treat a veterinary dermatologic condition, which in one embodiment is eczematoid dermatitis, chronic dermatitis, equine exuberant granuloma ("proud flesh"), decubitis ulcers, canine cutaneous granulomas ("lick" granuloma), and others that are known to one of ordinary skill in the art.

In one embodiment, the methods of the present invention may be used to treat a dermatologic condition in a subject anywhere on the body of the subject, including, inter alia, scalp, face, head, neck, shoulders, arms, elbows, behind the elbows, wrists, hands, fingers, palms, trunk, back, chest, shoulders, buttocks, genitals, legs, knees, behind the knees, feet, toes, ankles, soles, etc.

In one embodiment, the compounds for use in the present invention (for e.g., a lipid or phospholipid moiety bound to a physiologically acceptable monomer, dimer, oligomer, or polymer) are referred to herein as "Lipid-conjugates".

In one embodiment, Lipid-conjugates of the present invention prevent or treat a dermatologic condition. In another embodiment, Lipid-conjugates prevent and treat a skin hypersensitivity reaction. This is exemplified in Tables 1.1-1.4 and represents an embodiment of this invention. In another embodiment, Lipid-conjugates are effective in treating psoriasis, as exemplified in FIG. 1.2. In another embodiment, Lipid-conjugates are effective in treating contact dermatitis in humans, as exemplified in FIG. 1.2. In another embodiment, Lipid-conjugates decrease ear swelling in an animal model of skin hypersensitivity reaction, when administered i.p. (Table 1.1), s.c. (Table 1.2, and topically bilaterally (Table 1.3) or unilaterally (Table 1.4). In another embodiment, Lipid-conjugates inhibit proliferation of psoriatic skin fibroblasts and Swiss 3T3 cells (as exemplified in FIG. 1.1). In another embodiment, Lipid-conjugates decrease contact dermatitis scores (as exemplified in FIG. 1.2). In one embodiment, Compound XXVI (see compound descriptions hereinbelow) is useful to treat dermatologic conditions. In another embodiment, Compound XXVI decreases swelling after i.p. or s.c. administration, as exemplified in Tables 1.1 and 1.2, and inhibits the proliferation of cultured psoriatic skin fibroblasts and Swiss 3T3 cells, as exemplified in FIG. 1.1. In another embodiment, Compound XXIX (see compound descriptions hereinbelow) is useful to treat dermatologic conditions. In another embodiment, Compound XXIX decreases swelling after bilateral or unilateral topical administration, as exemplified in Tables 1.3 and 1.4. In another embodiment, Compound XXII (see compound descriptions hereinbelow) is useful to treat dermatologic conditions. In another embodiment, Compound XXII decreases contact dermatitis scores in patients after unilateral topical administration, as exemplified in FIG. 1.2.

In one embodiment, the invention provides a method for treating a subject with a dermatologic condition marked by unchecked inflammation, inappropriate cytokine response, or a combination thereof. In another embodiment, local cytokine profiles can be altered by the treatment according to the methods of the present invention. In one embodiment, the determination of the modulation of cytokines may be performed as described by U.S. application Ser. No. 10/952,496 filed Sep. 29, 2004, which is incorporated herein by reference in its entirety.

In another embodiment, the compounds for use in the present invention may be used to treat conditions secondary to dermatologic conditions, including sepsis and oxidative injury. The use of Lipid-conjugates to treat sepsis is demonstrated in U.S. application Ser. No. 10/627,981, filed Jul. 28, 2003, which is incorporated herein by reference in its entirety.

Administration of the Lipid-conjugates in a diversity of animal and cell models of disease invoked remarkable, and unexpected, cytoprotective effects, which, as exemplified herein, are useful in the prevention and treatment of dermatologic conditions and related diseases and/or conditions. Lipid-conjugates reduce ear swelling in mice induced by oxazolone, inhibit proliferation of cultured psoriatic skin fibroblasts and Swiss 3T3 cells, and reduce symptoms of contact dermatitis in humans (as exemplified in Example 1). In one embodiment, Lipid-conjugates may also prevent and/or treat dermatologic conditions via protecting against oxidative injury (as exemplified in Example 2) and via their membrane-stabilizing effects (as exemplified in Example 3). Finally, in one embodiment, Lipid-conjugates may prevent or treat dermatologic conditions via their $PLA_2$ enzyme inhibitory activity (as exemplified in Example 4).

The compounds for the use in the present invention also reduce sPLA2 expression in rat lung, reduce cysteinyl leukotrienes, reduce NO production, prevent airway remodeling, and reduce tumor necrosis factor-$\alpha$ (TNF-$\alpha$) in animal and cell models of obstructive respiratory disease; inhibit NO production, PGE2, sPLA2, and oleic acid release from PC12 and glial cells in cell models of CNS injury; reduce IL-8, Gro-$\alpha$, ena-78, and NF-$\kappa$B in an in vitro model of acute respiratory distress syndrome (as exemplified in U.S. application Ser. No. 10/952,496, which is incorporated by reference herein).

In one embodiment of the present invention, the useful pharmacological properties of the Lipid-conjugates, some of which are described hereinabove, may be applied for clinical use, and disclosed herein as methods for the prevention or treatment of a disease. The biological basis of these methods may be readily demonstrated by standard cellular and animal models of disease, for example, as described in the Examples 1-5, hereinbelow.

In one embodiment, the pharmacological activities of Lipid-conjugates, including membrane stabilization, anti-inflammation, anti-oxidant action, and attenuation of chemokine levels, may contribute to a Lipid-conjugate-treated cell's resistance to dermatologic conditions or diseases. In one embodiment, cell membrane stabilization may ameliorate or prevent tissue injury arising in the course of a dermatologic condition. In another embodiment, anti-oxidant action may limit oxidative damage to cell and blood components arising in the course of a dermatologic condition. In another embodiment, attenuation of chemokines levels may attenuate physiological reactions to stress that arise in the course of a dermatologic condition.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In one embodiment, the Lipid-conjugates of this invention possess a combination of multiple and potent pharmacological effects in addition to the ability to inhibit the extracellular form of the enzyme phospholipase A2. While the pharmacological activity of the Lipid-conjugates described herein may be due in part to the nature of the lipid moiety, the multiple and diverse combination of pharmacological properties observed for the Lipid-conjugates emerges from the ability of the compound structure to act essentially as several different drugs in one chemical entity.

In the cases described herein, the diversity of biological activities and the effectiveness in disease exhibited by the compounds for use in the present invention far exceed the properties anticipated by use of the starting materials themselves, when administered alone or in combination. However, the phospholipid conjugate compounds, alone or in combination, are valuable when used in the methods of treating diseases and conditions specifically described herein.

In one embodiment, methods of the present invention involve treating a subject by inter alia controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof.

In one embodiment of the invention, the term "controlling" refers to inhibiting the production and action of the above mentioned factors in order to maintain their activity at the normal basal level and suppress their activation in pathological conditions.

In one embodiment of the invention, a dermatologic condition is characterized by the presence of damaging agents, which comprise, inter alia, phospholipases, reactive oxygen species (ROS), free radicals, lysophospholipids, fatty acids or derivatives thereof, hydrogen peroxides, phospholipids, oxidants, cationic proteins, streptolysins, proteases, hemolysins, or sialidases.

Dosages and Routes of Administration

This invention encompasses administration of compounds as described herein or compositions comprising the same, for treating psoriasis, dermatitis, or other dermatologic conditions.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, a Lipid-conjugate used in the methods of this invention may be administered alone or within a composition. In another embodiment, compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

In another embodiment, they can also be combined where desired with other active agents, e.g., vitamins.

In one embodiment, the therapeutic compositions of the present invention comprise a Lipid-conjugate and one or more additional compounds effective in preventing or treating dermatologic conditions. In one embodiment, the additional compound is a moisturizer or an emollient, which in one embodiment is petrolatum, white petrolatum, hydrogenated vegetable oil, hydrophilic petrolatum, panthenol, primrose oil, omega-3 fish oils, omega-6 fish oils, linoleic acid, flax seed oil, ceramide, borage oil (linoleic acid), tocopherol (Vitamin E), tocopherol linoleate, dimethicone, glycerine or a combination thereof. In one embodiment, moisturizers improve the ability of the skin to absorb other administered compounds, including inter alia, the compounds for use in the present invention. In another embodiment, moisturizing agents minimize or prevent the skin from drying and cracking, thereby decreasing susceptibility of skin to environmental factors that generate free radicals, thereby preventing additional damage to the skin.

In another embodiment, the additional compound is a topical steroid, which in one embodiment is hydrocortisone, in one embodiment 1% hydrocortisone, triamcinolone, fluocinolone acetonide, halcinonide, halobetasol propionate, clobetasol propionate, betamethasone dipropionate, betamethasone valerate, and triamcinolone acetonide or a combination thereof; oral steroids; topical immunomodulators including, inter alia, tacrolimus, pimecrolimus, Ascomycin, cyclosporine, or a combination thereof; antihistamines, which in one embodiment is hydroxyzine or diphenhydramine hydrochloride, Ketotifen, Doxepin; biologics, which in one embodiment comprises Amevive (alefacept), Enbrel, Humira, Raptiva, Remicade, or a combination thereof; or a combination thereof. In another embodiment, the additional compound is an antibiotic, which in one embodiment comprise cloxacillin, cephalexin, penicillin, clindamycin or a combination thereof. In another embodiment, the additional compound is methotrexate, tar, coal tar, anthralin, dovonex, salicyclic acid, tazorac, moisturizers, aloe vera, soniatane, accutane, hydrea, mycophenolate mofetil, sulfasalazine, 6-thioguanine, or a combination thereof. In another embodiment, additional compounds comprise acyclovir, which in one embodiment is particularly effective in patients with eczema herpeticum. In one embodiment, additional compounds to treat seborrheic dermatitis comprise zinc pyrithione, selenium sulfide, sulfur, tar shampoo, flucinolone acetonide solution, triamcinolone acetonide lotion, ketoconazole cream, other imidazoles, or a combination thereof.

In another embodiment, the additional compound is an anti-inflammatory agent, which in one embodiment comprises aspirin, ibuprofen, ketoprofen, naproxen, or a combination thereof.

In another embodiment, the additional compound is an exfoliant, which in one embodiment comprises an enzymatic exfoliant or a mono- or -poly-hydroxy acid. In one embodiment, the exfoliant is an alpha-hydroxy acid, beta-hydroxy acid, tannic acid, glycolic acid, lactic acid, citric acid, salicylic acid, or a combination thereof. In another embodiment, the additional compound is an analgesic, or anesthetic, while in another embodiment it is aloe vera gel, aloe vera, licorice extract, pilewort, Canadian willow root, zinc, allantoin, or a combination thereof. In another embodiment, the additional compound is an anti-oxidant.

In another embodiment, the additional compound is an antibacterial, antifungal, antiviral, antihelminthic agent, or a combination thereof. In one embodiment, the additional compound is echinacea, golden seal, benzalkonium chloride, benzethonium chloride, iodine, grape seed extract, pomegranate extract, green tea extract or polyphenols, and the like, or combinations thereof. In one embodiment, an antihelminthic agent is metronidazole. In one embodiment, antiviral agent is acyclovir, tamvir, penciclovir, or a combination thereof. In one embodiment, the antibacterial agent is triclosan, neomycin, polymyxin, bacitracin, clindamycin, benzoyl peroxide, a tetracycline, a sulfa drug, a penicillin, a quinolone, a cephalosporin, or a combination thereof. In one embodiment, the antifungal agent is famesol, econazole, fluconazole, clotrimazole, ketoconazole, calcium or zinc undecylenate, undecylenic acid, butenafine hydrochloride, ciclopirox olaimine, miconazole nitrate, nystatin, sulconazole, terbinafine hydrochloride, and the like, or a combination thereof.

In one embodiment, the therapeutic compositions of the present invention are administered with other treatments that relieve symptoms. In one embodiment, other treatments comprise wet wrap bandaging, phototherapy, UV light exposure (UVA, UVB, or a combination thereof), psoralen plus UV-A (PUVA), UV-B 1 (narrow band UV-B) therapy, Balneotherapy, Climatotherapy, aromatherapy, relaxation, homeopathy, chinese herbal treatments, oil of evening primrose, and the like.

In one embodiment, the route of administration may be parenteral, enteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, body weight, and response of the individual patient, etc.

For topical application, particularly in the area around the eye, an admixture of the compounds with conventional creams, lotions, or delayed release patches is acceptable. Such a cream or lotion may comprise any agent described herein, and, in one embodiment, may be used to treat skin diseases and/or dermatologic conditions, such as, in one embodiment, contact dermatitis, atopic dermatitis, psoriasis, or a combination thereof.

Suitable dosage forms for topical administration include, but are not limited to, dispersions, lotions; creams; gels; pastes; powders; aerosol sprays; syrups or ointments on sponges or cotton applicators; and solutions or suspensions in an aqueous liquid, non-aqueous liquid, oil-in-water emulsion, or water-in-oil liquid emulsion. Because of its ease of administration, a cream, lotion, or ointment represents the most advantageous topical dosage unit form, in which case liquid pharmaceutical carriers may be employed in the composition. These creams, lotions, or ointments, may be prepared as rinse-off or leave-on products, as well as two stage treatment products for use with other skin cleansing or managing compositions. In a preferred embodiment, the compositions are administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

Ointment preparations may be roughly classified into fat/oil type ointments, emulsified ointments, water-soluble ointments and suspended ointments according to the type of the base (vehicle) used therefor. An ointment may comprise, for example, fats, fatty oils, lanolin, vaseline, paraffins, waxes, resins, plastics, glycols, higher alcohols, glycerol, water, emulsifiers, suspending agents or other appropriate additives as a diluent, carrier or as a vehicle. Manufacture of an ointment comprises, for example, adding the compound of the present invention to the appropriate additives, diluents, carriers or vehicles followed by mixing to make the mixture homogeneous.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein.

For enteral application, particularly suitable are tablets, dragees, liquids, drops, or capsules. In one embodiment, a sweetened vehicle is employed when a syrup, elixir, or the like is used for enteral application.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by dermatologic conditions. For example, compounds may be administered topically to treat dermatologic conditions. In another embodiment, the route of administration may be directed to a different organ or system than the one that is affected by dermatologic conditions. For example, compounds may be administered parenterally to treat dermatologic conditions. Thus, the present invention provides for the use of Lipid-conjugates in various dosage forms suitable for administration using any of the routes listed hereinabove.

In general, the doses utilized for the above described purposes will vary, but will be in an effective amount to exert the desired effect. As used herein, the term "pharmaceutically effective amount" refers to an amount of a compound of formulae A and I-LXXXVII as described hereinbelow, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. In one embodiment, a topical daily dose range, in single or divided doses, for the conditions described herein is from about 1 mg to 20,000 mg, more preferably about 2,000 mg to 16,000 mg, and most preferably about 6,000 mg to 10,000 mg of the active components (i.e., excluding excipients and carriers). When the compositions are dosed topically or intraocularly, they will generally be in a concentration range of from 0.1 to about 10% w/v, administered 1-4 times per day. In one embodiment, the compositions for use in the methods of the present invention are administered topically two times a day in a concentration of 1% and the following w/w % ratios: Water 70.0, Cetyl Alcohol, 10.6, Paraffin, White soft 10.6, Propylene Glycol 7.2, HyPE 1.0 and Sodium Dodecyl Sulfate 0.6 (as exemplified in Example 1.6).

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

The present invention has been illustrated in terms of the anti-disease activity of Lipid-conjugates and methods of their use as pharmaceutical compositions in the treatment of disease. The following sections present some examples of the therapeutic Lipid-conjugate compounds for use in the present invention and their chemical preparation.

Compounds

In one embodiment, the compounds for use in the present invention comprise a lipid or phospholipid moiety bound to a physiologically acceptable monomer, dimer, oligomer, or polymer. In one embodiment, the lipid compounds (Lipid-conjugates) for use in the present invention are described by the general formula:

[phosphatidylethanolamine-Y]n-X
[phosphatidylserine-Y]n-X
[phosphatidylcholine-Y]n-X
[phosphatidylinositol-Y]n-X
[phosphatidylglycerol-Y]n-X
[phosphatidic acid-Y]n-X
[lyso-phospholipid-Y]n-X
[diacyl-glycerol-Y]n-X
[monoacyl-glycerol-Y]n-X
[sphingomyelin-Y]n-X
[sphingosine-Y]n-X
[ceramide-Y]n-X
wherein Y is either nothing or a spacer group ranging in length from 2 to 30 atoms; and X is a physiologically acceptable monomer, dimer, oligomer or polymer; and n is the number of lipid molecules bound to a molecule of X, wherein n is a number from 1 to 1000.

In one embodiment, the invention provides low-molecular weight Lipid-conjugates, previously undisclosed and unknown to possess pharmacological activity, of the general formula described hereinabove. In another embodiment, wherein the general formula described hereinabove describes low-molecular weight Lipid-conjugates, X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, a polysaccharide, a hetero-polysaccharide, a homo-polysaccharide, a polypyranose, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment, X is conjugated to the lipid, phospholipid, or spacer via an ester bond. In another embodiment, X is conjugated to the lipid, phospholipid, or spacer via an amide bond.

As defined by the structural formulae provided herein for the Lipid-conjugates, these compounds may contain one to one thousand lipid moieties bound to a single physiologically acceptable polymer molecule. In one embodiment of this invention, n is a number from 1 to 1000. In another embodiment, n is a number from 1 to 500. In another embodiment, n is a number from 1 to 100. In another embodiment, n is a number from 2 to 1000. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain Lipid-conjugate products with either high or low ratios of lipid residues per polymer, as desired.

In one embodiment, the set of compounds comprising phosphatidylethanolamine covalently bound to a physiologically acceptable monomer, dimer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the Lipid-conjugates and the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

In one embodiment, Lipid-conjugate derivatives relevant to this invention are Lipid-conjugates wherein at least one of the fatty acid groups of the lipid moieties at position C1 or C2 of the glycerol backbone are substituted by a long chain alkyl group attached by amide, ether or alkyl bonds, rather than ester linkages.

In the methods, according to embodiments of the invention, the Lipid-conjugates administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the Lipid-conjugates moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or disaccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, a hetero-polysaccharide, a homo-polysaccharide, a polypyranose, polyglycan, protein, glycosaminoglycan, or a glycoprotein mixture. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In one embodiment, examples of polymers which can be employed as the conjugated moiety for producing Lipid-conjugates for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinylpyrrolidones, polysaccharides, polypyranoses, alginates, assimilable gums (e.g., xanthan gum), peptides, injectable blood proteins (e.g., serum albumin), cyclodextrin, and derivatives thereof.

In one embodiment, polysaccharides may be homo-polysaccharides, while in another embodiment, they may be hetero-polysaccharides.

In one embodiment, examples of monomers, dimers, and oligomers which can be employed as the conjugated moiety for producing Lipid-conjugates for use in the methods of the invention may be mono- or disaccharides, trisaccharides, oligopeptides, carboxylic acids, dicarboxylic acids, fatty acids, dicarboxylic fatty acids, salicylates, salicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of polysaccharides, polypyranoses, and/or glycosaminoglycans including heparins, heparan sulfates, hyaluronic acids, chondroitins, chondroitin sulfates, chondroitin-6-sulfates, chondroitin-4-sulfates, dermatins, dermatan sulfates, keratins, keratan sulfates, or dextrans.

In some cases, according to embodiments of the invention, the monomer or polymer chosen for preparation of the Lipid-conjugate may in itself have select biological properties. For example, both heparin and hyaluronic acid are materials with known physiological functions. In the present invention, however, the Lipid-conjugates formed from these substances as starting materials display a new and wider set of pharmaceutical activities than predicted from the administration of either heparin or hyaluronic acid that are not covalently linked to a phospholipid. It can be shown, by standard comparative experiments as described below and in U.S. application Ser. No. 10/952,496, incorporated herein by reference, that phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), or to hydroxyethylstarch (Compound XXVIII), are far superior in terms of potency and range of useful pharmaceutical activity to the free conjugates (the polymers above and the like). In fact, these latter substances are, in general, not considered useful in methods for treatment of most of the diseases described herein, including the treatment of dermatologic conditions. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active Lipid-conjugates described herein can have a wide range of molecular weights, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a Lipid-conjugate devoid of the desired biological activity, or lead to chemical or physiological instability to the extent that the Lipid-conjugate is rendered useless as a drug in the method of use described herein.

In one embodiment, the compound for use in the present invention is represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is dextran. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, the compound for use in the present invention is represented by the structure of the general formula (I):

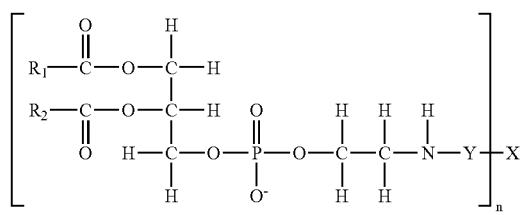

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer or a physiologically acceptable polymer; and
n is a number from 1 to 1,000;
wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

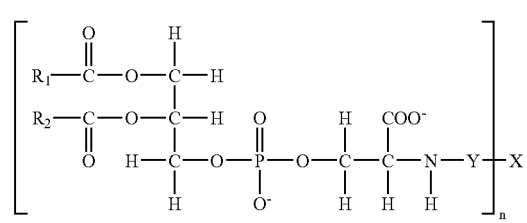

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a physiologically acceptable monomer, dimer, oligomer or polymer wherein X is a glycosaminoglycan; and n is a number from 1 to 1000;

wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the COO⁻ moiety of the phosphatidylserine.

In another embodiment, the compound for use in the present invention is represented by the structure of the general formula (III):

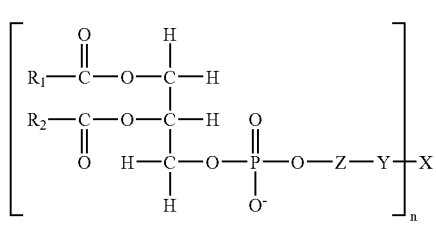

(III)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000;
wherein any bond between the phosphatidyl, Z, Y and X is either an amide or an esteric bond.

In another embodiment, the compound for use in the present invention is represented by the structure of the general formula (IV):

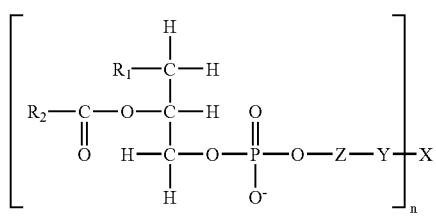

(IV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (V):

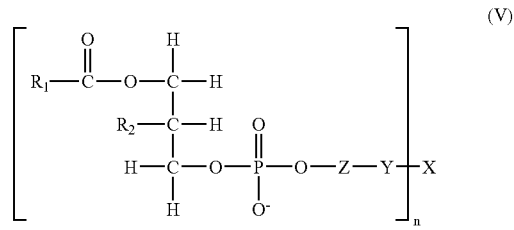

(V)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (VI):

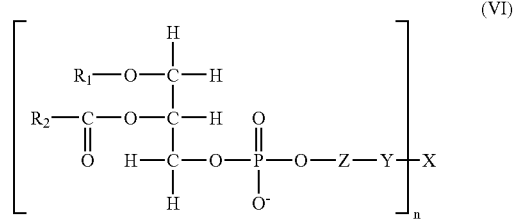

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a physiologically acceptable monomer, dimer, oligomer, or polymer wherein X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (VII):

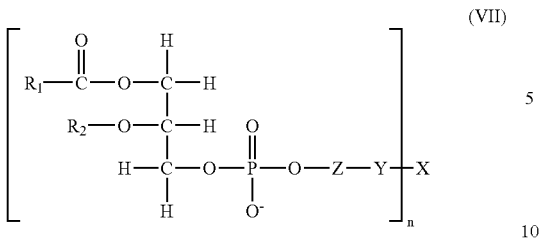

(VII)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 1000;
- wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound for use in the present invention is represented by the structure of the general formula (VIII):

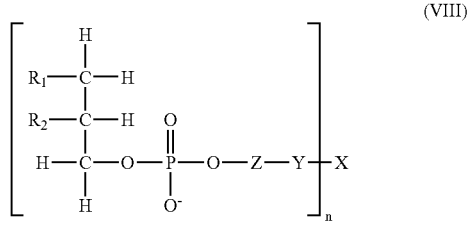

(VIII)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IX):

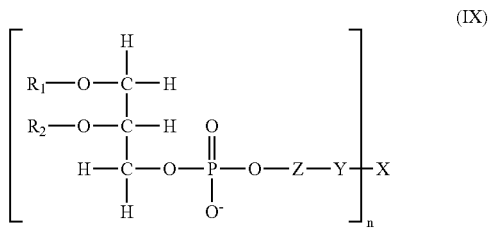

(IX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IXa):

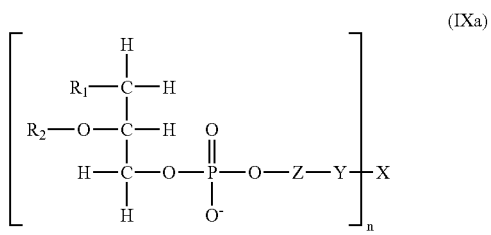

(IXa)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 1000;
- wherein any bond between the phospholipid, Z, Y and X is either an amide or an esteric bond.

In another embodiment, the compound for use in the present invention is represented by the structure of the general formula (IXb):

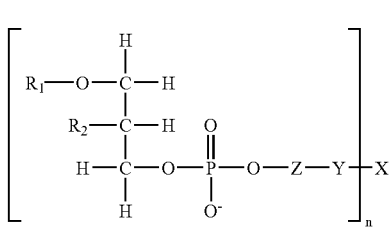

(IXb)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (X):

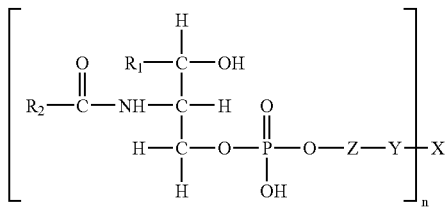

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 1000;

wherein any bond between the ceramide phosphoryl, Z, Y and X is either an amide or an esteric bond.

In another embodiment, the compound for use in the present invention is represented by the structure of the general formula (XI):

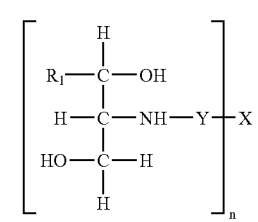

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XII):

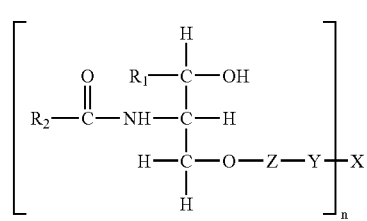

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein any bond between the ceramide, Z, Y and X is either an amide or an esteric bond.

In another embodiment, the compound for use in the present invention is represented by the structure of the general formula (XIII):

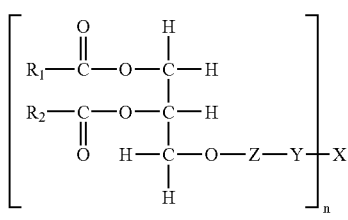

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein any bond between the diglyceryl, Z, Y and X is either an amide or an esteric bond.

In another embodiment, the compound for use in the present invention is represented by the structure of the general formula (XIV):

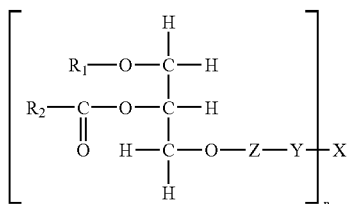

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XV):

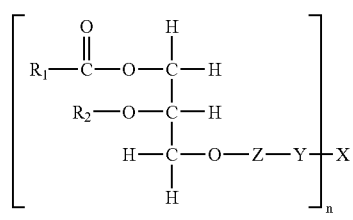

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XVI):

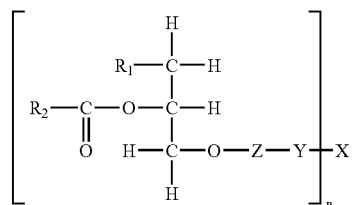

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVII):

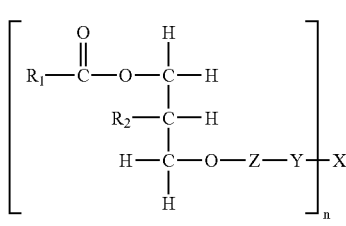
(XVII)

wherein
  $R_1$ is either hydrogen or a linear, saturated, mono-unsaturated, or poly-unsaturated, alkyl chain ranging in length from 2 to 30 carbon atoms;
  $R_2$ is a linear, saturated, mono-unsaturated, or poly-unsaturated, alkyl chain ranging in length from 2 to 30 carbon atoms;
  Z is either nothing, choline, phosphate, inositol, or glycerol;
  Y is either nothing or a spacer group ranging in length from 2 to 30 atoms;
  X is a physiologically acceptable monomer, dimer, oligomer or polymer wherein X is a glycosaminoglycan; and
  n is a number from 1 to 1000;
  wherein any bond between the lipid, Z, Y and X is either an amide or an esteric bond.

In another embodiment, the compound for use in the present invention is represented by the structure of the general formula (XVIII):

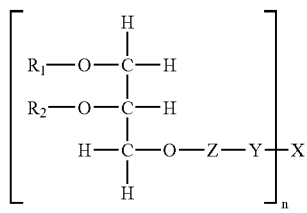
(XVIII)

wherein
  $R_1$ is either hydrogen or a linear, saturated, mono-unsaturated, or poly-unsaturated, alkyl chain ranging in length from 2 to 30 carbon atoms;
  $R_2$ is either hydrogen or a linear, saturated, mono-unsaturated, or poly-unsaturated, alkyl chain ranging in length from 2 to 30 carbon atoms;
  Z is either nothing, choline, phosphate, inositol, or glycerol;
  Y is either nothing or a spacer group ranging in length from 2 to 30 atoms;
  X is a physiologically acceptable monomer, dimer, oligomer or polymer wherein X is a glycosaminoglycan; and
  n is a number from 1 to 1000;
  wherein any bond between the lipid, Z, Y and X is either an amide or an esteric bond.

In another embodiment, the compound for use in the present invention is represented by the structure of the general formula (XIX):

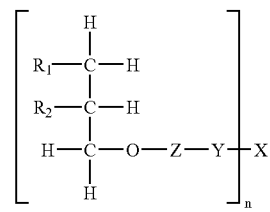
(XIX)

wherein
  $R_1$ is either hydrogen or a linear, saturated, mono-unsaturated, or poly-unsaturated, alkyl chain ranging in length from 2 to 30 carbon atoms;
  $R_2$ is either hydrogen or a linear, saturated, mono-unsaturated, or poly-unsaturated, alkyl chain ranging in length from 2 to 30 carbon atoms;
  Z is either nothing, choline, phosphate, inositol, or glycerol;
  Y is either nothing or a spacer group ranging in length from 2 to 30 atoms;
  X is a physiologically acceptable monomer, dimer, oligomer or polymer wherein X is a glycosaminoglycan; and
  n is a number from 1 to 1000;
  wherein any bond between the lipid, Z, Y and X is either an amide or an esteric bond.

In another embodiment, the compound for use in the present invention is represented by the structure of the general formula (XX):

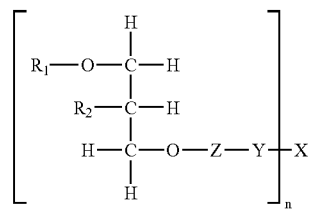
(XX)

wherein
  $R_1$ is either hydrogen or a linear, saturated, mono-unsaturated, or poly-unsaturated, alkyl chain ranging in length from 2 to 30 carbon atoms;
  $R_2$ is either hydrogen or a linear, saturated, mono-unsaturated, or poly-unsaturated, alkyl chain ranging in length from 2 to 30 carbon atoms;
  Z is either nothing, choline, phosphate, inositol, or glycerol;
  Y is either nothing or a spacer group ranging in length from 2 to 30 atoms;
  X is a physiologically acceptable monomer, dimer, oligomer or polymer wherein X is a glycosaminoglycan; and
  n is a number from 1 to 1000;
  wherein any bond between the lipid, Z, Y and X is either an amide or an esteric bond.

In another embodiment, the compound for use in the present invention is represented by the structure of the general formula (XXI):

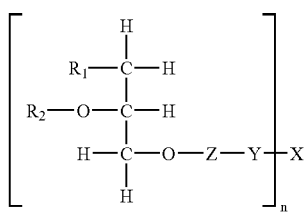

(XXI)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, choline, phosphate, inositol, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 1000;
- wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. According to this aspect and in one embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
|---|---|---|---|
| PE | None | Hyaluronic acid (2–2000 kDa) | XXII |
| Dimyristoyl-PE | None | Hyaluronic acid | XXIII |
| PE | None | Heparin (0.5–110 kDa) | XXIV |
| PE | None | Chondroitin sulfate A | XXV |
| PE | None | Carboxymethylcellulose (20–500 kDa) | XXVI |
| PE | Dicarboxylic acid + Diamine | Polygeline (haemaccel) (4–40 kDa) | XXVII |
| PE | None | Hydroxyethylstarch | XXVIII |
| PE | Dicarboxylic acid + Diamine | Dextran (1–2,000 kDa) | XXIX |
| PE | None | Aspirin | XXX |
| PE | Carboxyl amino group | Hyaluronic acid (2–2000 kDa) | XXXI |
| PE | Dicarboxyl group | Hyaluronic acid (2–2000 kDa) | XXXII |
| PE | Dipalmitoic acid | Hyaluronic acid (2–2000 kDa) | XXXIII |
| PE | Carboxyl amino group | Heparin (0.5–110 kDa) | XXXIV |

TABLE 1-continued

| Phospholipid | Spacer | Polymer (m.w.) | Compound |
|---|---|---|---|
| PE | Dicarboxyl group | Heparin (0.5–110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20–500 kDa) | XXXVIII |
| PE | Dicarboxyl group | Carboxymethylcellulose (20–500 kDa) | XXXIX |
| PE | None | Polygeline (haemaccel) (4–40 kDa) | XL |
| PE | Carboxyl amino group | Polygeline (haemaccel) (4–40 kDa) | XLI |
| PE | Dicarboxyl group | Polygeline (haemaccel) (4–40 kDa) | XLII |
| PE | Carboxyl amino group | Hydroxyethylstarch | XLIII |
| PE | Dicarboxyl group | Hydroxyethylstarch | XLIV |
| PE | None | Dextran (1–2,000 kDa) | XLV |
| PE | Carboxyl amino group | Dextran (1–2,000 kDa) | XLVI |
| PE | Dicarboxyl group | Dextran (1–2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2–2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl- hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |

In one embodiment of the invention, the compounds for use in the present invention are any one or more of Compounds I-LXXXVIII. In another embodiment, the compounds for use in the present invention are Compound XXII, Compound XXIII, Compound XXIV, Compound XXV, Compound XXVI, Compound XXVII, Compound XXVII, Compound XXIX, Compound XXX, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment of this invention, low molecular weight Lipid-conjugates are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, CO-alkylene-NH—, cycloalkylene, wherein alkylene in each instance, is straight or branched chain and contains 2 or more, preferably 2 to 18 carbon atoms in the chain, —(—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these Lipid-conjugates provide wide-range protection from diverse injurious processes, and are effective in amelioration of diseases that requires cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, the invention provides a pharmaceutical composition for treating a subject suffering from a dermalogic disorder, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from a dermalogic disorder, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

Preparation of Compounds for Use in the Present Invention

In one embodiment, the preparation of high molecular weight Lipid-conjugates for use in the methods of the present invention is as described in U.S. Pat. No. 5,064,817, which is incorporated fully herein by reference. In one embodiment, these synthetic methods are applicable to the preparation of low molecular weight Lipid-conjugates as well, which in one embodiment are Lipid-conjugates comprising monomers and dimers as the conjugated moiety, with appropriate modifications in the procedure as would be readily evident to one skilled in the art. The preparation of some low molecular weight Lipid-conjugates may be conducted using methods well known in the art or as described in U.S. patent application Ser. No. 10/952,496, which is incorporated herein by reference in its entirety.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

The abbreviations used in the examples below are:
PE=phosphatidyl-ethanolamine
HA=hyaluronic acid
Cpd=Compound
Cpd XXII=dipalmitoyl-PE conjugated to HA
Cpd XXIII=dimyristoyl-phosphatidyl-ethanolamine linked to HA
Cpd XXIV=PE conjugated to heparin
Cpd XXV=PE conjugated to chondroitin sulfate A (CSA)
Cpd XXVI=PE conjugated to carboxymethyl cellulose (CMC)
Cpd XXIX=PE conjugated to dextran
Cpd XXX=PE conjugated to aspirin
Cpd LXXXVIII=PE conjugated to glutaryl
The compounds used in the examples below were prepared as described in U.S. patent application Ser. No. 10/952,496, which is fully incorporated herein by reference.

Example 1

Skin diseases, Contact Dermatitis and Psoriasis

Contact dermatitis is a widespread skin disease and is often attributed to a delayed type hypersensitivity response. Cutaneous, or skin, hypersensitivity reactions may occur in response to virtually any material and may present clinically in either acute or chronic forms. A widely-accepted system for invoking the delayed type hypersensitivity response is systemic sensitization to an antigen followed by its local application. Psoriasis is another common form of dermatitis marked by plaque-like formations, evident on extensor surfaces. As a hyperproliferative disorder of epithelial cells, drug therapies are typically examined in cell cultures obtained from sufferers of the condition.

Both secreted (sPLA) and cytosolic (cPLA) PLA2 have been identified in human skin. Their inflammatory roles have been determined in patients suffering from inflammatory skin diseases such as psoriasis, although some also play a role in maintaining healthy skin integrity.

Experiments 1.1-1.4 demonstrate that treatment of the animals afflicted with a hypersensitivity reaction readily respond to the administration of Lipid-conjugates, whether applied intraperitoneally (Table 1.1), subcutaneously (Table 1.2), or topically (Tables 1.3-1.4), as both prophylactic and acute therapy.

Treatment Groups: In Experiments 1.1-1.2, "late sensitized only" mice were given topical application of oxazolone to both sides of one ear 24 hours before measuring its swelling, while fully sensitized mice were treated with topical application of oxazolone to their shaved stomachs, and then on day 6, with topical application of oxazolone to both sides of one ear. In Experiments 1.3-1.4, treatment was as described above, except that oxazolone was applied to both sides of both ears.

Measurement of swelling: Swelling was measured in 0.1 mm increments by subtracting the ear width of each individual mouse before treatment from the width after treatment. Percent inhibition was calculated by the net swelling of treated fully-sensitized ears (over that of the control group A), divided by the net swelling of vehicle-treated fully-sensitized ears.

In Experiment 1.1, mice were injected intraperitoneally daily from day 0 until day 6 with vehicle (saline) or treatment compounds (40 mg CMC, 40 mg Compound XXVI, or 5 mg betamethasone, in saline).

TABLE 1.1

Attenuation of Dermal Delayed Type Hypersensitivity Response by Intraperitoneally Administered Lipid-Conjugate

| Group | Treatment | No. of Mice | Swelling (ear width after sensitization − ear width before sensitization)[a] | Percent inhibition |
|---|---|---|---|---|
| A | Control (late sensitized) | 6 | 1.8 ± 1.0 | — |
| B | Fully sensitized + saline | 6 | 18.5 ± 0.97 | — |
| C | Fully sensitized + carrier polymer (CMC) (0.4 μmol/kg) | 6 | 19.8 ± 1.13 | — |
| D | Fully sensitized + Cpd XXVI (0.4 μmol/kg) | 6 | 7.9 ± 1.37 | 66 |
| E | Fully sensitized + betamethasone (15 μmol/kg) | 6 | 6.5 ± 1.35 | 74 |

[a]Data are presented as mean ± S.D.

In Experiment 1.2, mice were injected subcutaneously adjacent to the oxazolone-challenged area, 3 h before application of oxazolone to the ear and 1 h after application of oxazolone to the ear with vehicle (saline) or treatment compounds (40 mg CMC, 40 mg Compound XXVI, or 1 mg betamethasone, in saline).

TABLE 1.2

Attenuation of Dermal Delayed Type Hypersensitivity Response by Subcutaneously Adminstered Lipid-Conjugate

| Group | Treatment | No. of Mice | Swelling (ear width after sensitization − ear width before sensitization)[a] | Percent inhibition |
|---|---|---|---|---|
| A | Control (late sensitized) | 5 | 4.1 ± 0.82 | — |
| B | Fully sensitized + saline | 5 | 18.3 ± 0.82 | — |
| C | Fully sensitized + carrier polymer (CMC) (0.4 μmol/kg) | 5 | 13.5 ± 2.17 | 35 |
| D | Fully sensitized + Cpd XXVI (0.4 μmol/kg) | 5 | 5.9 ± 1.52 | 87 |
| E | Fully sensitized + betamethasone (3 μmol/kg) | 5 | 8.1 ± 1.19 | 72 |

[a] Data are presented as mean ± S.D.

In Experiment 1.3, mice were treated topically on both ears over the challenged area daily beginning day 0 until day 6 with vehicle or treatment compounds (20 μL of 0.1% Compound XXIX or dextran in 50% EtOH or 20 μl of Dermovat (steroid ointment)).

Experiment 1.5 demonstrates that Lipid-conjugates effectively inhibit the proliferation of cultured psoriatic skin fibroblasts and Swiss 3T3 cells. Fibroblasts of human psoriatic skin (dermis) cells, (full circles) or Swiss 3T3 cells (empty circles) were treated with Compound XXVI at the indicated

TABLE 1.3

Attenuation of Dermal Delayed Type Hypersensitivity Response by Bilateral Topical Administration of Lipid Conjugate

| Group | Treatment | No. of Mice | Swelling (ear width after sensitization − ear width before sensitization) [a] | Percent inhibition |
|---|---|---|---|---|
| A | Control (late sensitized only) | 5 | 1.5 ± 0.70 | — |
| B | Fully sensitized + saline | 5 | 24.3 ± 1.56 | — |
| C | Fully sensitized + carrier polymer (dextran) (0.5 μmol/kg) | 5 | 24.4 ± 2.4 | — |
| D | Fully sensitized + Compound XXIX (0.5 μmol/kg) | 5 | 12.17 ± 1.52 | 53 |
| E | Fully sensitized + Dermovat (3 μmol/kg) | 5 | 10.6 ± 0.84 | 60 |

[a] Data are presented as mean ± S.D.

In Experiment 1.4, mice were treated topically with vehicle or treatment compounds (20 μL of 0.1% Compound XXIX in 50% EtOH or 20 μl of Dermovat (steroid ointment)) on only one of the oxazolone-challenged ears 5 times 4-6 hours following the oxazolone challenge.

concentration for three days, after which the cells were counted (FIG. 1.1). The cell number of the control, untreated group at the end of the three day incubation was taken as 100%. For comparison, carboxymethylcellulose was tested alone (data not shown).

TABLE 1.4

Attenuation of Dermal Delayed Type Hypersensitivity Response by Unilateral Topical Administration of Lipid-Conjugate

| | | | Swelling (ear width after sensitization − ear width before sensitization) [a] | | | Percent inhibition | |
|---|---|---|---|---|---|---|---|
| Group | Treatment | No. of mice | Left ear | Both ears | Right ear | Left ear | Right ear |
| A | Late sensitized only | 10 | | 1.0 ± 2.0 | | — | — |
| B | Fully sensitized + vehicle | 10 | | 23.0 ± 4.0 | | — | — |
| C | Fully sensitized + Compound XXIX (0.5 μmol/kg), on right ear only | 7 | 20.0 ± 1.0 | | 11.0 ± 1.0 | 14 | 46 |
| D | Fully sensitized + Dermovat (3 μmol/kg) on right ear only | 7 | 7.0 ± 1.0 | | 7.0 ± 1.0 | 63 | 63 |

[a] Data are presented as mean ± S.D.

As shown in Tables 1.1-1.4, treatment with the Lipid-conjugates reduced ear swelling in mice showing a delayed-type hypersensitivity (DTH) response to oxazolone. The results presented in Table 1.4 demonstrate that although the topical administration of oxazolone was unilateral in both cases, the steroid affected both ears, while the topically applied Lipid-conjugate affected only the area to which it was applied, indicating that the Lipid-conjugate acts locally rather than systemically in this model, which may reduce potential side effects seen with treatments that show systemic infiltration.

Experiment 1.6: To show that Lipid-conjugates are effective in treating patients with contact dermatitis, a double-blind, placebo-controlled study was conducted in patients with contact dermatitis.

Drug Preparation:

A topical preparation of 1% Compound XXII (MW-50 kDa) was prepared by the Hadassah pharmacy (Jerusalem, Israel) using the following w/w % ratios: Water 70.0, Cetyl Alcohol, 10.6, Paraffin, White soft 10.6, Propylene Glycol 7.2, HyPE 1.0 and Sodium Dodecyl Sulfate 0.6.

Study Design and Experimental Procedures:

The study group comprised a total of 11 female patients aged 19-50 (mean age: 34.6). All the patients had received a clinical diagnosis of contact dermatitis and a positive patch test to at least a single allergen. The disease distribution was symmetrical in all patients at the study sites. All patients exhibited contact dermatitis on the surface of their hands with some patients exhibiting the disease on their forearms as well. Patients refrained from any systemic treatment for no less than a month before the intitation of the study and from topical treatment for no less than two weeks before the study. Disease severity was evaluated before treatment (day 0) and after a month of treatment (day 30) by the physician assessment scoring criteria (ranging from 0 to 3) described in Table 1.5. In the initial analysis, the scores for each criteria were assigned and summed to give a total score for each patient, with a minimum possible severity score of 0 and a maximum possible severity score of 15. The range of severity scores for patients in the initial evaluation was 8-15.

TABLE 1.5

Physician assessment scoring criteria for contact dermatitis

| Dryness | 0-none | 3-very dry |
| Scaling | 0-none | 3-severe scaling |
| Redness (erythema) | 0-none | 3-severe redness |
| Pruritus (itching) | 0-none | 3-very pruritic |
| Fissures | 0-none | 3-deep fissures |

Each patient received two color-coded tubes of cream. One tube contained the active pharmaceutical ingredient (Compound XXII), and the other tube contained just the vehicle (placebo). Except for their label color, the tubes were identical in size, and the tube contents were identical in color and odor. The doctor and the patients were unaware of which tube contained the Compound XXII. Patients were instructed to consistently apply cream twice a day. They were instructed to apply the cream from the blue marked tube to their right hand and forearm and to apply cream from the pink marked tube to their left hand and forearm. The same doctor evaluated the patients before and after treatment. The study was approved by the Helsinki Committee of Israeli Ministry of Health based on animal safety data presented.

All 11 enrolled patients completed the one month study. The mean total score before treatment was 11.27±0.71. After one month of unilateral treatment with the lipid conjugate, marked differences were visible between the right and left hands and arms of the patients. On the Compound XXII-treated side, the average visual score was reduced by 69.9%, while on the placebo-treated side, the average visual score was reduced by 32.9% ($p<0.005$) (FIG. 1.2).

These experiments demonstrate that Lipid-conjugates are effective remedies for the management of various forms of dermatitis including skin hypersensitivity reactions and contact dermatitis.

Example 2

Anti-Oxidant Therapy

There is evidence that allergic and inflammatory skin diseases like atopic dermatitis, urticaria and psoriasis are mediated by oxidative stress, which damages cellular proteins, lipids, and DNA, leading to membrane dysfunction and instability. Conversely, patients with dermatitis may be more susceptible to oxidative stress because of damaged skin may function as a weakened barrier. The skin is particularly susceptible because it is exposed to endogenous and environmental pro-oxidant agents, leading to the harmful generation of reactive oxygen species (ROS). The noxious effect of ROS, such as peroxide free radicals, on living tissue is known as oxidative stress or damage.

In order to determine the effect of Lipid-conjugates on oxidative damage to proteins or cell membranes, tissue was exposed to hydrogen peroxide ($H_2O_2$) produced by (a) the enzyme glucose oxidase (GO) in the absence or presence of additional membrane destabilizing agents such as $PLA_2$ or (b) by exposure to divalent cations, such as copper.

Experiments 2.1-2.3 demonstrate the ability of Lipid-conjugates to preserve cells from oxidative damage, as judged by the cells' retention of both arachidonic acid and of low molecular weight intracellular substances.

Experiment 2.1: Confluent BGM (green monkey kidney epithelial) cells were labeled with $^3$H-arachidonic acid. The cells were treated with Compound XXVI for 30 min prior to treatment with GO and $PLA_2$ (0.5 U/ml) (FIG. 2.1).

Experiment 2.2: BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generator) for 90 min, and the culture medium was collected and counted for $^{35}S$ radioactivity. For treatment with Compound XXVI, cells were incubated with 3 or 10 μM Compound XXVI for 30 min prior to introduction of GO. Data are presented as mean±SEM for 5 replications. *$p<0.005$;$p<0.001$ (FIG. 2.2**).

Experiment 2.3 demonstrates the ability of Lipid-conjugates to inhibit the oxidation of blood lipoprotein. Low density lipoprotein (LDL; 0.1 μM) and or hydroperoxides (LOOH) were incubated in the absence and presence of various concentrations of Compound XXII or HA at 37° C. At time zero, 5 μM $CuCl_2$ was added to the dispersions, and the mixtures were continuously monitored for oxidation products at 245 nm (FIG. 2.3). The absorbance at 245 (OD units) is depicted as a function of time.

These experiments demonstrate that administration of Lipid-conjugates is an effective therapy to prevent tissue damage induced by oxidative stress (associated with free radical and hydrogen peroxide production) by a plurality of mechanisms, including inhibiting the oxidation of lipoprotein, inhibiting arachidonic acid release, and preserving the integrity of cell membranes (inhibiting GAG degradation), including red blood cell membranes, as described below. The efficacy of Lipid-conjugates in protecting against tissue damage induced by oxidative stress may contribute to their usefulness in preventing or treating dermatitis.

Example 3

Hemolysis

Hemolysis, which in one embodiment, is the breakdown of red blood cells (RBC), may be either a primary disease in itself, or a syndrome associated with another disease or physiological insult. In order to determine the effect of Lipid-conjugates on hemolysis, red blood cells were incubated in the presence of known membrane destabilizing agents and the release of hemoglobulin into the extracellular medium was detected.

Experiment 3.1 demonstrates that the Lipid-conjugates serve to maintain the stability of human red blood cells exposed to membrane-destroying agents. Human RBC were washed in saline and suspended in Hanks buffer (pH 7.4). Hemolysis was induced in the absence or presence of 10 μM Lipid-conjugates by treatment with either 5 U/ml streptolysin O (SLO), 25 U/ml streptolysin S (SLS), or 5 μg/ml lysophosphatidylcholine (lyso-PC) for 20 min. The cell membranes were spun and the hemoglobin content in the supernatant was determined by measuring the O.D. at 540 nm (Table 3.1).

TABLE 3.1

Prevention of Hemolysis by Compound XXII, Compound XXVI and Compound XXIV

| Lipid-conjugate | HEMOLYSIS (O.D. AT 540 nm) | | |
|---|---|---|---|
| | SLO | SLS | Lyso-PC |
| None | 1.000 | 1.000 | 1.000 |
| HA | 1.000 | 1.000 | 1.875 |
| Compound XXII-30* | 0.650 | 0.750 | 0.335 |
| Compound XXII-60* | 0.012 | 0.005 | 0.017 |
| Compound XXII-110* | 0.005 | 0.002 | 0.012 |
| Compound XXIV | 0.002 | 1.100 | 0.002 |
| Compound XXVI-60* | 0.012 | 0.005 | 0.002 |
| Compound XXVI-110* | 0.002 | | 0.002 |

*The number expresses the amount of nmoles lipid conjugated to 1 mg of polymer.

These experiments demonstrate that the Lipid-conjugates are effective therapy in the treatment of cell membrane rupture and/or hemolysis. Thus, Lipid-conjugates protect against membrane destabilization, which may be a mechanism through which they are useful for the methods of the present invention. For example, Lipid-conjugates may protect against membrane destabilization that may lead to skin damage or dermatitis.

Example 4

PLA$_2$ Inhibition

The PLA$_2$ enzymes catalyze the hydrolysis of fatty acids attached to phospholipids on the plasma membrane. Arachidonic acid, the main metabolite released from these reactions, is a precursor for other enzymatic reactions mediated by lipoxygenases and cyclooxygenases. These reactions produce prostaglandins and leukotrienes, which have a profound effect on inflammation in vivo. Therefore, PLA$_2$ inhibitors are capable of inhibiting inflammation via their ability to inhibit the production of downstream inflammatory factors.

Experiment 4.1 was designed to determine the effect of Compound XXII, Compound XXV, Compound XXX, and Compound LXXXVIII on the inhibition of the Naja Naja Snake Venom PLA$_2$ enzyme in an in vitro fluorometric assay. The reaction of the PLA$_2$ enzyme and the PLA$_2$ enzyme substrate 2-(6-(7-nitrobenz-2-oxa-1,3diazol-4-yl)amino) hexanoyl-1-hexadecanoyl-sn-glycero-3-phosphocholine (NHGP) yields a product, which can be detected using a fluorometer. Decreased absorbance indicates inhibition of the PLA$_2$ enzyme.

Methods

Compound XXII and Compound XXV were solubilized and diluted in D-PBS, and tested at final concentrations of 0.625, 0.125, 0.25, 0.5 and 1 mg/ml. Compound XXX and Compound LXXXVIII were solubilized in 100% dimethyl sulfoxide (DMSO), diluted in D-PBS and tested at final concentrations of 0.01, 0.1 and 1 mg/ml. 1 mM NHGP was diluted in D-PBS, for a final concentration of 1 μM. The positive control, Mefenamic Acid (Sigma, M-4267), was tested at a final concentration of 0.1 mg/ml. The PLA$_2$ enzyme is derived from the Naja Naja Snake Venom (Sigma, P6139) and tested at a final concentration of 5 Units/ml. The reaction was carried out in 200 μl solution and initiated by addition of substrate. Fluorescence was read immediately and then every minute for 30 minutes for a total of 30 readings. The fluorometer was set as follows: Excitation 450/50; Emission 530/25; Gain 50.

Results

Compound XXII inhibited the PLA$_2$ enzyme by 37%, 42%, 71% and 98% at 0.125, 0.25, 0.5 and 1 mg/ml respectively (FIG. 4.1A) compared to 41% inhibition by 0.1 mg/ml mefenamic acid, which served as a positive control. Compound XXV inhibited the PLA$_2$ enzyme, although with no apparent dose response, by 20%, 30% and 26% at 0.625, 0.125, 0.25 mg/ml (FIG. 4.1B). The inhibition of the PLA$_2$ enzyme by Compound LXXXVIII and Compound XXX could not be determined in this assay, due to difficulties in solubilizing the compounds in DMSO, even after sonication.

Thus, Compound XXII inhibits the PLA$_2$ enzyme in a dose-dependent manner, indicating its ability to act as an anti-inflammatory drug. Other experiments showing anti-inflammatory effects of Lipid-conjugates are demonstrated in U.S. application Ser. No. 10/952,496 filed Sep. 29, 2004 and are hereby incorporated by reference.

Example 5

Toxicity Tests

Toxicity is a measure to the degree to which a compound or substance is deleterious to an organism. Toxicological effects are generally dose-dependent. A therapeutic compound that is non-toxic, even at high doses, would have an advantage over other compounds.

In Experiment 5.1, the Lipid-conjugates Compound XXII, Compound XXIV, Compound XXV and Compound XXVI were evaluated for toxicity. Toxicity was evaluated in mice (3/group) one week after a single i.p. dose of 1000, 500 or 200 mg/kg of Lipid-conjugates. Mortality rate, body weight, blood count (red and white cells), hematocrit, and internal organ histology after sacrifice were assessed. These parameters were compared in Lipid-conjugate-treated and in control, untreated mice. Treatment with Lipid-conjugates did not alter the parameters described above, with the exception of Compound XXIV, which induced hemorrhage.

Tables 5.1 and 5.2 depict the non-toxicity of Compound XXII as demonstrated in acute (Table 5.1) and long-term (Table 5.2) toxicity tests.

TABLE 5.1

Results of acute (7 day) toxicity test - Compound XXII

| Dose of Compound XXI (mg/kg body weight) | Body weight (g) | | RBC × 10$^6$ | WBC × 10$^3$ | Hematocrit % |
|---|---|---|---|---|---|
| | Start | Final | | | |
| 0 (control) | 21.9 ± 0.2 | 22.6 ± 0.3 | 10.7 ± 0.4 | 9.3 ± 0.3 | 45.0 ± 0.5 |
| 250 | 22.1 ± 0.4 | 23.1 ± 0.6 | 11.4 ± 0.1 | 7.7 ± 0.2 | 43.3 ± 0.7 |
| 500 | 21.4 ± 0.3 | 22.3 ± 0.4 | 11.5 ± 0.3 | 8.1 ± 1.3 | 44.7 ± 2.3 |
| 1000 | 21.7 ± 0.2 | 22.1 ± 0.2 | 10.9 ± 0.4 | 7.4 ± 0.6 | 40.3 ± 0.7 |

RBC=red blood cells; WBC=white blood cells. Data are presented as mean±SEM.

For the long-term toxicity test, a group of 6 mice received an i.p injection of 100 mg Lipid-conjugate (Compound XXII)/kg body weight 3 times a week for 30 weeks (e.g., 180 mg total to a mouse weighing 20 g). Toxicity was evaluated as for Table 5.1. The results of the long-term toxicity test are depicted in Table 5.2. There were no incidents of mortality and no significant changes in body weight, red or white blood cell count, or hematocrit induced by this treatment compared to control, untreated mice.

TABLE 5.2

Results of long-term (30 weeks) toxicity test - Compound XXII

| Dose of Compound XXII (mg/kg body weight, 3 times/week for 30 weeks) | Body weight (g) Final | RBC × $10^6$ | WBC × $10^3$ | Hematocrit % |
|---|---|---|---|---|
| 0 (control) | 39.5 ± 3.1 | 10.9 ± 0.8 | 9.3 ± 0.6 | 45.0 ± 0.8 |
| 100 | 39.0 ± 2.7 | 11.7 ± 0.7 | 8.1 ± 15 | 43.4 ± 4.9 |

In Experiment 5.2, Compounds XXII and XXV were evaluated for toxicity after intravenous (i.v.) administration. Toxicity was evaluated in Sprague-Dawley rats (5/group) five days after a four daily injections into the tail of approximately 100 mg/kg of Lipid-conjugates or vehicle (PBS). Five days after the final injection, rats were anesthetized under isoflourane, the abdomen was opened, blood was collected by heart puncture, urine was collected from the bladder, and organs were collected into formalin. All animals were subjected to a full necropsy following sacrifice, including examination of the external surface of the body, all orifices, and the cranial, thoracic and abdominal cavities and their contents.

All organs/tissues listed in Tables 5.3 and 5.4 were fixed and preserved in a 4% formaldehyde solution for at least a 48-hr fixation period. In addition, any other organs/tissues with gross macroscopic changes were preserved as well in 4% formaldehyde solution. The preparation of slides for histopathology evaluation was performed by PAI, Maryland (Project 03-1273). Histopathological changes were described and scored, using semiquantitative grading consisting of five grades (0-4) that reflect the severity of the changes (0=unremarkable, 1=minimal, 2=mild, 3=moderate, 4=marked).

Hematological, Biochemical and Urine Evaluation

Results demonstrated that neither Compound XXII nor Compound XXV indicated toxic effects on any of the systems or organs examined (Tables 5.3, 5.4. and 5.5). All parameters were within the known normal range for this strain and age or were not significantly different from the control group.

TABLE 5.3

Effect of i.v. Compound XXII and Compound XXV administration on hematological parameters

HEMATOLOGY

| | Male | | | Female | | | |
|---|---|---|---|---|---|---|---|
| | Cpd XXII (n = 5) | Cpd XXV (n = 5) | Control (n = 5) | Cpd XXII (n = 5) | Cpd XXV (n = 5) | Control (n = 5) | Expected Ranges |
| WBC (×10E3/μL) | 7.68 ± 2.18 | 6.20 ± 1.74 | 6.70 ± 3.54 | 4.43 ± 2.25 | 4.26 ± 0.77 | 5.62 ± 1.03 | 5–18 |
| RBC (×10E3/μL) | 7.68 ± 0.35 | 7.50 ± 0.25 | 7.29 ± 0.33 | 7.47 ± 0.26 | 7.52 ± 0.48 | 7.51 ± 0.63 | 5–8.5 |
| HgB (g/dl) | 15.28 ± 0.78 | 14.34 ± 0.51 | 14.22 ± 0.62 | 14.78 ± 0.61 | 14.12 ± 0.72 | 14.54 ± 1.29 | 10–16 |
| HCT (%) | 49.28 ± 2.85 | 47.58 ± 1.83 | 46.02 ± 2.13 | 44.80 ± 2.23 | 45.14 ± 2.37 | 45.28 ± 4.35 | 35–50 |
| MCV (fl) | 64.16 ± 2.28 | 63.42 ± 0.69 | 63.22 ± 3.22 | 59.94 ± 1.71 | 60.02 ± 1.37 | 60.40 ± 2.86 | 50–75 |
| MCH (pg) | 19.88 ± 0.62 | 19.08 ± 0.25 | 19.50 ± 0.86 | 19.76 ± 0.57 | 18.78 ± 0.29 | 19.36 ± 0.50 | 15–20 |
| MCHC (g/dl) | 30.98 ± 0.41 | 30.08 ± 0.26 | 30.86 ± 0.43 | 32.96 ± 0.74 | 31.32 ± 0.51 | 32.08 ± 1.44 | 30–36 |
| RDW (%) | 15.40 ± 0.47 | 16.10 ± 0.67 | 15.84 ± 0.84 | 13.72 ± 0.54 | 13.76 ± 0.34 | 14.14 ± 0.60 | 12–16 |
| HDW | 2.56 ± 0.06 | 2.57 ± 0.07 | 2.57 ± 0.08 | 2.60 ± 0.06 | 2.54 ± 0.10 | 2.59 ± 0.13 | 1.7–2.5 |
| PLT (×10E3/μL) | 851.40 ± 154.66 | 927.20 ± 232.63 | 877.0 ± 56.69 | 755.20 ± 166.63 | 910.6 ± 275.53 | 952.80 ± 125.66 | 900–1500 |
| MPV (fl) | 4.82 ± 0.53 | 4.82 ± 0.54 | 5.46 ± 0.32 | 4.86 ± 0.37 | 4.86 ± 0.18 | 5.34 ± 0.44 | 4–60 |
| NEUT (%) | 10.20 ± 1.30 | 15.80 ± 7.82 | 12.40 ± 5.41 | 15.00 ± 4.80 | 13.40 ± 5.68 | 9.80 ± 2.77 | 20–50 |
| LYMP (%) | 87.20 ± 1.30 | 80.00 ± 7.38 | 84.20 ± 5.89 | 81.40 ± 4.34 | 82.40 ± 6.35 | 86.60 ± 4.28 | 58–108 |
| MONO (%) | 2.40 ± 0.55 | 3.00 ± 1.22 | 3.20 ± 1.30 | 1.60 ± 1.34 | 2.80 ± 0.84 | 2.44 ± 1.89 | 0–8 |
| EOS (%) | 0.20 ± 0.45 | 1.20 ± 1.30 | 2.20 ± 4.92 | 1.80 ± 0.45 | 1.40 ± 1.34 | 0.80 ± 0.45 | 0–5 |
| BASO (%) | 0.00 ± 0.00 | 0.00 ± 0.00 | 0.00 ± 0.00 | 0.20 ± 0.45 | 0.00 ± 0.00 | 0.00 ± 0.00 | 0–1 |

Data are presented as mean ± std. dev.

TABLE 5.4

Effect of i.v. Compound XXII and Compound XXV administration on biochemical blood parameters

BIOCHEMISTRY

| | Male | | | Female | | | |
|---|---|---|---|---|---|---|---|
| | Cpd XXII (n = 5) | Cpd XXV (n = 5) | Control (n = 5) | Cpd XXII (n = 5) | Cpd XXV (n = 5) | Control (n = 5) | Expected Ranges |
| Glu (mg/dL) | 164.60 ± 29.91 | 202.00 ± 83.30 | 125.20 ± 22.95 | 124.40 ± 19.17 | 176.80 ± 35.58 | 176.60 ± 33.29 | 104.5–291.7 |
| Chol (mg/dL) | 101.80 ± 6.76 | 95.00 ± 18.14 | 96.00 ± 11.38 | 90.80 ± 5.97 | 105.80 ± 16.22 | 93.00 ± 15.81 | 30.46–107.8 |
| UREA (mg/dL) | 38.56 ± 4.84 | 39.00 ± 4.95 | 41.80 ± 8.17 | 37.20 ± 4.97 | 33.80 ± 8.11 | 36.60 ± 5.55 | 21.6–40.3 |
| ALB (g/dL) | 3.30 ± 0.10 | 3.46 ± 0.29 | 3.40 ± 0.12 | 3.54 ± 0.11 | 3.76 ± 0.23 | 3.70 ± 0.28 | 2.5–3.7 |
| ALP (u/L) | 292.80 ± 51.74 | 336.00 ± 77.08 | 309.20 ± 74.45 | 202.00 ± 36.86 | 176.00 ± 20.33 | 194.80 ± 32.70 | |
| ALT (u/L) | 47.80 ± 8.17 | 58.60 ± 7.44 | 55.00 ± 11.42 | 48.60 ± 6.91 | 50.00 ± 6.96 | 48.60 ± 8.56 | 21.8–102.6 |

TABLE 5.4-continued

Effect of i.v. Compound XXII and Compound XXV administration on biochemical blood parameters

| | BIOCHEMISTRY | | | | | | |
|---|---|---|---|---|---|---|---|
| | Male | | | Female | | | |
| | Cpd XXII (n = 5) | Cpd XXV (n = 5) | Control (n = 5) | Cpd XXII (n = 5) | Cpd XXV (n = 5) | Control (n = 5) | Expected Ranges |
| AST (u/L) | 126.60 ± 11.97 | 110.60 ± 29.31 | 109.40 ± 19.72 | 123.40 ± 18.42 | 116.00 ± 49.20 | 91.00 ± 7.11 | 73.9–160.6 |
| AMYL (u/L) | 2722.60 ± 167.25 | 2599.20 ± 503.23 | 2774.00 ± 121.72 | 1787.20 ± 106.83 | 1644.00 ± 182.62 | 1766.40 ± 240.51 | 1935.7–3271.88 |
| Ca (mg/dL) | 10.76 ± 0.88 | 8.74 ± 2.12 | 8.82 ± 1.37 | 10.06 ± 0.92 | 10.66 ± 0.18 | 10.06 ± 1.11 | 6–10.6 |
| CPK (u/L) | 555.60 ± 185.54 | 410.00 ± 273.20 | 536.00 ± 252.86 | 536.40 ± 191.27 | 308.00 ± 62.69 | 282.00 ± 84.59 | 339–1513 |
| CREA (mg/dL) | 0.53 ± 0.14 | 0.38 ± 0.09 | 0.37 ± 0.03 | 0.56 ± 0.04 | 0.49 ± 0.05 | 0.34 ± 0.15 | 0.34–0.57 |
| Pi (mg/dL) | 11.36 ± 1.49 | 10.21 ± 0.87 | 10.51 ± 1.14 | 10.05 ± 0.62 | 9.58 ± 1.71 | 8.26 ± 0.92 | 5.89–8.27 |
| TRIG (mg/dL) | 110.20 ± 41.70 | 82.00 ± 29.49 | 140.80 ± 44.57 | 65.60 ± 14.17 | 68.60 ± 29.36 | 42.60 ± 13.43 | |
| PROT (g/dL) | 5.50 ± 0.14 | 5.84 ± 0.34 | 5.76 ± 0.38 | 5.60 ± 0.00 | 6.50 ± 0.25 | 6.30 ± 0.48 | 5.3–9.7 |
| Globulins (g/dL) | 2.20 ± 0.14 | 2.38 ± 0.24 | 2.36 ± 0.45 | 2.06 ± 0.11 | 2.74 ± 0.15 | 2.60 ± 0.31 | 2.09–6.8 |
| Alb/Glob (ratio) | 1.48 ± 0.13 | 1.46 ± 0.21 | 1.50 ± 0.32 | 1.72 ± 0.15 | 1.38 ± 0.13 | 1.44 ± 0.19 | |
| T. BIL (mg/dL) | 0.12 ± 0.04 | 0.13 ± 0.05 | 0.17 ± 0.05 | 0.10 ± 0.00 | 0.18 ± 0.04 | 0.14 ± 0.05 | 0.04–0.24 |
| GGT (u/L) | 0.00 ± 0.54 | 0.00 ± 0.00 | 0.00 ± 0.00 | 0.04 ± 0.09 | 0.00 ± 0.00 | 0.00 ± 0.00 | |
| LDH (u/L) | 24.29 ± 13.32 | 20.01 ± 18.70 | 20.41 ± 10.32 | 27.61 ± 21.44 | 16.61 ± 4.43 | 13.68 ± 2.39 | 24.6–68.6 |
| Cl (mmol/L) | 99.60 ± 2.07 | 101.00 ± 2.35 | 106.00 ± 4.53 | 101.80 ± 1.92 | 102.80 ± 3.11 | 107.20 ± 4.97 | 79.4–111.3 |
| K (mmol/L) | 6.24 ± 0.79 | 6.26 ± 0.78 | 6.08 ± 1.36 | 6.26 ± 1.53 | 5.32 ± 0.38 | 5.80 ± 0.32 | 4–8 |
| Na (mmol/L) | 147.60 ± 1.14 | 142.00 ± 1.58 | 137.60 ± 6.58 | 146.00 ± 2.92 | 140.20 ± 4.02 | 141.20 ± 1.79 | 135–155 |

Data are presented as mean ± std. dev.

TABLE 5.5

Effect of i.v. Compound XXII and Compound XXV administration on urinalysis results

| | URYNALYSIS | | | | | |
|---|---|---|---|---|---|---|
| | Male | | | Female | | |
| | Cpd XXII (n = 5) | Cpd XXV (n = 5) | Control (n = 5) | Cpd XXII (n = 5) | Cpd XXV (n = 5) | Control (n = 5) |
| Glu | — | — | — | — | — | — |
| BIL | — | — | — | — | — | — |
| Ketones | — | — | — | — | — | — |
| S.G. | 1.04 ± 0.01 | 1.03 ± 0.01 | 1.04 ± 0.01 | 1.04 ± 0.01 | 1.03 ± 0.01 | 1.04 ± 0.02 |
| Eryth | — | — | — | — | — | — |
| pH | 6.60 ± 1.55 | 6.80 ± 0.45 | 6.80 ± 0.84 | 6.20 ± 0.45 | 7.00 ± 0.82 | 6.60 ± 0.55 |
| T.S | 6.88 ± 2.09 | 6.40 ± 2.12 | 8.22 ± 1.96 | 7.88 ± 4.00 | 6.13 ± 1.66 | 7.80 ± 4.01 |
| Leuk | — | — | — | — | — | — |

Data are presented as mean ± std. dev.

Macroscopic Evaluation

In addition, no macroscopic abnormalities were reported.

Histopathological Assessment

For Compound XXV, no treatment-related changes in histopathological assessment were noted (Table 5.6). For Compound XXII, treatment-related changes were limited to the injection site (Table 5.7). These changes were of minimal grade and consisted of subcutaneous mononuclear cell infiltration and fibrosis. The mononuclear cell infiltration was not limited to perivascular localization and therefore is not indicative of immunological reaction to the test compound. It is suggested that during the injection of the test compound, a minimal dose was deposited in the subcutis, provoking a very minimal and limited inflammatory cell infiltration, which should not be considered as an adverse reaction. In addition, in two animals, one male and one female, foreign body (hair shaft) minimal inflammation was noted. This change, although seen only in treated groups, is suggested to be caused by needle trauma and is not considered to be related to the test compound. Other observed changes had comparable incidence in control and treated groups or are known to occur frequently in untreated rats of the same age and strain, and therefore are considered to be of no relation to the test compound. Such changes consisted of mononuclear cell infiltration in the liver and presence of renal basophilic tubules.

TABLE 5.6

Effect of i.v. Compound XXV treatment on histopathology of specific organs.

| | Compound XXV-treated | | | | | | | | | | Control, PBS-treated | | | | | | | | | |
|---|---|---|---|---|---|---|---|---|---|---|---|---|---|---|---|---|---|---|---|---|
| | Males | | | | | Females | | | | | Males | | | | | Females | | | | |
| Brain | 0 | 0 | 0 | 0 | 0 | 0 | 0 | 0 | 0 | 0 | 0 | 0 | 0 | 0 | 0 | 0 | 0 | 0 | 0 | 0 |
| Thymus | 0 | 0 | 0 | 0 | 0 | 0 | 0 | 0 | 0 | 0 | 0 | 0 | 0 | 0 | 0 | 0 | 0 | 0 | 0 | 0 |

TABLE 5.6-continued

Effect of i.v. Compound XXV treatment on histopathology of specific organs.

| | Compound XXV-treated | | Control, PBS-treated | |
|---|---|---|---|---|
| | Males | Females | Males | Females |
| Esophagus | 0 0 0 0 0 | 0 0 0 M 0 | 0 0 0 0 0 | 0 0 0 0 0 |
| Pancreas | 0 0 0 0 0 | 0 0 0 0 0 | 0 0 0 0 0 | 0 0 0 0 0 |
| Liver Mononuclear cell infiltration Periportal acute inflammation | 0 0 0 0 0 | 0 0 1 0 0 | 0 0 0 0 0 | 0 0 0 0 0 |
| Spleen | 0 0 0 0 0 | 0 0 0 0 0 | 0 0 0 0 0 | 0 0 0 0 0 |
| Adrenal | 0 0 0 0 0 | 0 0 0 0 0 | 0 0 0 0 0 | 0 0 0 0 0 |
| Lungs | 0 0 0 0 0 | 0 0 0 0 0 | 0 0 0 0 0 | 0 0 0 0 0 |
| Stomach | 0 0 0 0 0 | 0 0 0 0 0 | 0 0 0 0 0 | 0 0 0 0 0 |
| Heart | 0 0 0 0 0 | 0 0 0 0 0 | 0 0 0 0 0 | 0 0 0 0 0 |
| Aorta | 0 0 0 0 0 | 0 0 0 0 0 | 0 0 0 0 0 | 0 0 0 0 0 |
| Kidneys Cortex-basophilic tubules | 0 1 1 1 1 1 | 0 0 1 1 | 0 1 1 1 1 | 0 0 0 1 |
| Duodenum | 0 0 0 0 0 | 0 0 0 0 0 | 0 0 0 0 0 | 0 0 0 0 0 |
| Jejunum | 0 0 0 0 0 | 0 0 0 0 0 | 0 0 0 0 0 | 0 0 0 0 0 |
| Ileum | 0 0 0 0 0 | 0 0 0 0 0 | 0 0 0 0 0 | 0 0 0 0 0 |
| Colon | 0 0 0 0 0 | 0 0 0 0 0 | 0 0 0 0 0 | 0 0 0 0 0 |
| Testes/Ovary | 0 0 0 0 0 | 0 0 0 0 0 | 0 0 0 0 0 | 0 0 0 0 0 |
| Epididymides/Uterus | 0 0 0 0 0 | 0 0 0 0 0 | 0 0 0 0 0 | 0 0 0 0 0 |
| Injection site (tail) | 0 0 | 0 0 0 0 0 | 0 0 0 0 0 | 0 0 0 0 |
| Subcutis - foreign body (hair shaft) granulomatous inflammation | 1 1 1 | 1 | | |
| Subcutis - Mononuclear cell infiltration | | 1 | | |
| Subcutis - Fibrosis | | | | |

TABLE 5.7

Effect of i.v. Compound XXII treatment on histopathology of specific organs.

| | Compound XXII-treated | | Control, PBS-treated | |
|---|---|---|---|---|
| | Males | Females | Males | Females |
| Brain | 0 0 0 0 0 | 0 0 0 0 0 | 0 0 0 0 0 | 0 0 0 0 0 |
| Thymus | 0 0 0 0 0 | 0 0 0 0 0 | 0 0 0 0 0 | 0 0 0 0 0 |
| Esophagus | 0 0 M 0 0 | 0 0 0 M 0 | 0 0 0 0 0 | 0 0 0 0 0 |
| Pancreas | 0 0 0 0 0 | 0 0 0 0 0 | 0 0 0 0 0 | 0 0 0 0 0 |
| Liver Mononuclear cell infiltration Periportal acute inflammation | 1 0 0 0 0 | 1 0 0 0 0 | 0 0 0 0 0 | 0 0 0 0 0 |
| Spleen | 0 0 0 0 0 | 0 0 0 0 0 | 0 0 0 0 0 | 0 0 0 0 0 |
| Adrenal | 0 0 0 0 0 | 0 0 0 0 0 | 0 0 0 0 0 | 0 0 0 0 0 |
| Lungs | 0 0 0 0 0 | 0 0 0 0 0 | 0 0 0 0 0 | 0 0 0 0 0 |
| Stomach | 0 0 0 0 0 | 0 0 0 0 0 | 0 0 0 0 0 | 0 0 0 0 0 |
| Heart | 0 0 0 0 0 | 0 0 0 0 0 | 0 0 0 0 0 | 0 0 0 0 0 |
| Aorta | 0 0 0 0 0 | 0 0 0 0 0 | 0 0 0 0 0 | 0 0 0 0 0 |
| Kidneys Cortex-basophilic tubules | 1 0 1 0 | 1 1 1 1 1 | 0 1 0 1 1 1 1 | 0 0 1 |
| Duodenum | 0 0 0 0 0 | 0 0 0 0 0 | 0 0 0 0 0 | 0 0 0 0 0 |
| Jejunum | 0 0 0 0 0 | 0 0 0 0 0 | 0 0 0 0 0 | 0 0 0 0 0 |
| Ileum | 0 0 0 0 0 | 0 0 0 0 0 | 0 0 0 0 0 | 0 0 0 0 0 |
| Colon | 0 0 0 0 0 | 0 0 0 0 0 | 0 0 0 0 0 | 0 0 0 0 0 |
| Testes/Ovary | 0 0 0 0 0 | 0 0 0 0 0 | 0 0 0 0 0 | 0 0 0 0 0 |
| Epididymides/Uterus | 0 0 0 0 0 | 0 0 0 0 0 | 0 0 0 0 0 | 0 0 0 0 0 |
| Injection site (tail) | 0 | 0 | 0 0 | 0 0 0 |
| Subcutis - foreign body (hair shaft) granulomatous inflammation | 1 | 1 | | |

TABLE 5.7-continued

Effect of i.v. Compound XXII treatment on histopathology of specific organs.

| | Compound XXII-treated | | | | Control, PBS-treated | | | |
|---|---|---|---|---|---|---|---|---|
| | Males | | Females | | | Males | | Females |
| Subcutis - Mononuclear cell infiltration | 1 | 1 | 1 | 1 | 1 | 1 | 1 | |
| Subcutis - Fibrosis | 1 | | 1 | 1 | | 1 | | |

TABLE 5.8

Toxicity Test Results

| Dose (mg/injection) | MK835 Survival (%) | MK865 Survival (%) |
|---|---|---|
| 0 | 100 | 100 |
| 0.6 | 100 | 100 |
| 2 | 66 | 100 |
| 6 | 33 | 66 |

Thus, the Lipid-conjugates have very low toxicity, as indicated in short and long-term toxicity tests.

What is claimed is:

1. A method of treating a dermatologic condition in a human subject, comprising the step of administering to said subject a compound represented by the structure of the general formula (I):

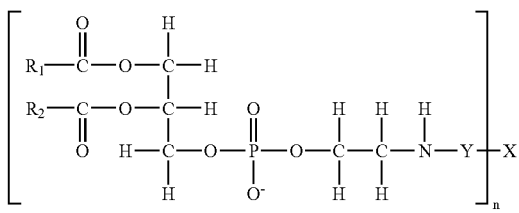

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is nothing;
wherein the phospholipid moiety is directly linked to X via an amide bond;
X is hyaluronic acid having intact sugar rings; and
n is a number from 2 to 1000;
and/or a pharmaceutically acceptable salt or a pharmaceutical product thereof.

2. The method according to claim 1, wherein $R_1$ and $R_2$ are both palmitoyl moieties.

3. The method according to claim 1, wherein $R_1$ and $R_2$ are both myristoyl moieties.

4. The method according to claim 1, wherein said dermatologic condition is psoriasis.

5. The method according to claim 1, wherein said dermatologic condition is contact dermatitis.

6. The method according to claim 1, wherein said dermatologic condition is atopic dermatitis.

7. A method of treating a dermatologic condition in a subject, comprising the step of administering to said subject a compound represented by the structure of the general formula (III):

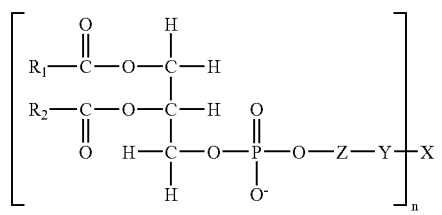

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, ethanolamine, serine, inositol, choline, or glycerol;
Y is nothing;
X is a glycosaminoglycan having intact sugar rings; and
n is a number from 2 to 1000;
and/or a pharmaceutically acceptable salt or a pharmaceutical product thereof.

8. The method according to claim 7, wherein said glycosaminoglycan is hyaluronic acid.

9. The method according to claim 7, wherein said glycosaminoglycan is heparin.

10. The method according to claim 7, wherein said glycosaminoglycan is chondroitin sulfate.

11. The method according to claim 7, wherein $R_1$ and $R_2$ are both palmitoyl moieties.

12. The method according to claim 7, wherein $R_1$ and $R_2$ are both myristoyl moieties.

13. The method according to claim 7, wherein said dermatologic condition is psoriasis.

14. The method according to claim 7, wherein said dermatologic condition is contact dermatitis.

15. The method according to claim 7, wherein said dermatologic condition is atopic dermatitis.

16. The method according to claim 7, wherein said subject is a human.

17. The method according to claim 1, wherein n is a number from 2 to 100.

18. The method according to claim 1, wherein the molecular weight of said hyaluronic acid is from 5000 to 10,000 Daltons.

19. The method according to claim 1, wherein the molecular weight of said hyaluronic acid is from 10,000 to 20,000 Daltons.

20. The method according to claim 7, wherein n is a number from 2 to 100.

21. The method according to claim 7, wherein the molecular weight of said glycosaminoglycan is from 5000 to 10,000 Daltons.

22. The method according to claim 7, wherein the molecular weight of said glycosaminoglycan is from 10,000 to 20,000 Daltons.

* * * * *